US005656452A

United States Patent [19]

Rao et al.

[11] Patent Number: 5,656,452

[45] Date of Patent: Aug. 12, 1997

[54] NF-$AT_P$, A T LYMPHOCYTE DNA-BINDING PROTEIN

[75] Inventors: Anjana Rao; Patrick Gerald Hogan, both of Cambridge; Patricia McCaffrey, Newton; Jugnu Jain, Natick, all of Mass.

[73] Assignees: President and Fellows of Harvard College, Cambridge; Dana-Farber Cancer Institute, Inc., Boston, both of Mass.

[21] Appl. No.: 145,006

[22] Filed: Oct. 29, 1993

Related U.S. Application Data

[63] Continuation-in-part of Ser. No. 17,052, Feb. 11, 1993, abandoned, which is a continuation-in-part of Ser. No. 6,067, Jan. 15, 1993, abandoned.

[51] Int. Cl.$^6$ .......................... C12N 15/13; C12N 15/63; C12P 21/00; C12Q 1/68

[52] U.S. Cl. .......................... 435/69.1; 435/6; 435/252.3; 435/254.11; 435/320.1; 435/325; 435/358; 435/365; 536/23.5; 536/24.31

[58] Field of Search .................................. 536/23.5, 24.3, 536/24.31; 435/320.1, 240.2, 69.1, 6

[56] References Cited

U.S. PATENT DOCUMENTS 5,162,209 11/1992 Scheele ................................ 435/91.41

FOREIGN PATENT DOCUMENTS

WO93/04203 3/1993 WIPO .

OTHER PUBLICATIONS

Broome S., et al., "Immunological screening method to detect specific translation products", 1978, *Proc. Natl. Acad. Sci. USA*, 75:2746–2749.

Woodrow, M., et al., "p21$^{ras}$ and Calcineurin Synergize to Regulate the Nuclear Factor of Activated T Cells", 1993, *J. Exp. Med.*, 178:1517–1522.

Yaseen, N.R., et al., "Comparative Analysis of NFAT (Nuclear Factor of Activated T Cells) Complex in Human T and B Lymphocytes", *J. Biological Chem.*, 268:14285–14293.

Ullman et al., "Transmission of Signals from the T Lymphocyte Antigen Receptor to the Genes Responsible for Cell Proliferation and Immune Function", 1990, *Ann. Rev. Immunol.*, vol. 8, pp. 421–452.

Flanagan et al., "Nuclear Association of a T–Cell Transcription Factor Blocked by FK–506 and Cyclosporin A", 1991, *Nature*, vol. 352, pp. 803–807.

Jain et al., "Nuclear Factor of Activated T Cells Contains Fos and Jun", 1992, *Nature*, vol. 356 pp. 801–804.

Jain et al., "Analysis of the AP–1 Sites in the IL–2 Promoter", 1992, *J. Immunol.*, vol. 148, pp. 1240–1250.

Klee et al., "Calcineurin", 1988, *Advances in Enzymology, Cornell Univ. Medical College, NY, NY; Interscience Publication*, vol. 61, pp. 149–200.

Fruman et al., "Calcineurin Phosphatase Activity in T Lymphocytes is Inhibited by FK 506 and Cyclosporin A", 1992, *Proc. Natl. Acad. Sci. USA*, vol. 89, pp. 3686–3690.

Liu et al., "Calcineurin Is a Common Target of Cyclophilin–Cyclosporin A and FKBP–FK506 Complexes", 1991, *Cell*, vol. 66, pp. 807–815.

Schreiber et al., "The Mechanism of Action of Cyclosporin A and FK506", 1992, *Immunology Today*, vol. 13, No. 4, pp. 136–142.

Sambrook et al., "Hybridization and Autoradiography" *Molecular Cloning: A Laboratory Manual*, Second Edition, 1989, Cold Spring Harbor Press, Cold Spring Harbor, NY, p. 7.52.

Kretzschmar et al., "Transcriptional Regulation of the HIV–1 Promoter by NF–kB In Vitro", 1992, *Genes and Development*, vol. 6, pp. 761–774.

*Current Protocols in Molecular Biol.*, F.M. Ausubel, Ed. §5.3, Green Publishing Associates and Wiley Interscience, NY, 1989.

Diamond et al., "Transcription Factor Interactions: Selectors of Positive or Negative Regulation From a Single DNA Element", 1990, *Science*, vol. 249, pp. 1266–1272.

Rao et al., "Activation Specificity of Arsonate–Reactive T Cell Clones", 1984, *J. Exp. Med.*, vol. 159, pp. 479–494.

Kubo et al., "Characterization of the Monoclonal Antibody Which Detects all Murine αβ T Cell Receptors", 1989, *J. Immunol.*, vol. 142, pp. 2736–2742.

McCaffrey et al., "A T Cell Nuclear Factor Resembling NF–AT Binds to an NF–kB Site and to the Conserved Lymphokine Promoter Sequence 'Cytokine–1'", 1992, *J. Biol. Chem.*, vol. 267, No. 3, pp. 1864–1871.

Larson et al., "A High–Capacity Column for Affinity Purification of Sequence–Specific DNA–Binding Proteins", 1992, *Nucleic Acids Research*, vol. 20, p. 3525.

Valge–Archer, V.E., et al., "Transformation of T Lymphocytes by the v–fos Oncogene", 1990, *J. Immunol.*, vol. 145, pp. 4355–4364.

King et al., "Chemical Modification of the Calmodulin–Stimulated Phosphatase, Calcineurin, by Phenylglyoxal", 1987, *J. Biol. Chem.*, vol. 262, pp. 10658–10662.

Baeuerle et al., "Activation of DNA–Binding Activity in an Apparently Cytoplasmic Precursor of the NF–kB Transcription Factor", 1988, *Cell*, vol. 53, pp. 211–217.

Serfling et al., "Ubiquitous and Lymphycyte–Specific Factors are Involved in the Induction of the Mouse Interleukin 2 Gene in T Lymphocytes", 1989, *EMBO J.*, vol. 8, pp. 465–473.

Jamieson et al., "Physiologic Activation of T Cells Via the T Cell Receptor Induces NF–kB", 1991, *J. Immuno.*, vol. 147, pp. 416–420.

Briggs et al., "Purification and Biochemical Characterization Of the Promoter–Specific Transcription Factor, Spl", 1986, *Science*, vol. 234, pp. 47–52.

(List continued on next page.)

*Primary Examiner*—Charles L. Patterson, Jr.
*Assistant Examiner*—Eric Grimes
*Attorney, Agent, or Firm*—Fish & Richardson, P.C.

[57] ABSTRACT

Isolated nucleic acids encoding the NF-$AT_p$ protein, a T lymphocyte DNA binding protein.

16 Claims, 20 Drawing Sheets

OTHER PUBLICATIONS

Verweij et al., "Cell Type Specificity and Activation Requirements for NFAT–1 (Nuclear Factor of Activated T–cells) Transcriptional Activity Determined by a New Method Using Transgenic Mice to Assay Transcriptional Activity of an Individual Nuclear Factor", 1990, *J. Biol. Chem.*, vol. 265, pp. 15788–15795.

Jain et al., "Analysis of the Preexisting and Nuclear Forms of Nuclear Factor of Activated T Cells", 1993, *J. Immunol.*, vol. 151, pp. 837–848.

Riegel, et al., "Nuclear Events After Activation of CD4+8+ Thymocytes", 1990, *J. Immunol.*, vol. 144, pp. 3611–3617.

Hashimoto et al., "Identification of an Autoinhibitory Domain in Calcineurin", 1990, *J. Biol. Chem.*, vol. 265, pp. 1924–1927.

Altschul et al., "Basic Local Alignment Search Took", 1990, *J. Mol. Biol.*, vol. 215, pp. 403–410.

Kerpolla et al., "Fos is a Preferential Target of Glucocorticoid Receptor Inhibition of AP–1 Activity in Vitro", 1993, *Mol. Cell. Biol.*, vol. 13, pp. 3782–3791.

Boise et al., "The NFAT–1 DNA Binding Complex in Activated T Cells Contains Fra–1 and JunB", Mar. 1993, *Mol. Cell. Biol.*, vol. 13, No. 3, pp. 1911–1919.

Clipstone et al., "Identification of Calcineurin as a Key Signalling Enzyme in T–lymphocyte Activation", 1992, *Nature*, vol. 357, pp. 695–697.

Cockerill et al., "The Granulocyte–macrophage Colony–stimulating Factor/Interleukin 3 Locus is Regulated by an Indicible Cyclosporin A–sensitive Enhancer", 1993, Proc. Natl. Acad. Sci. USA, vol. 90, pp. 2466–2470.

Granelli–Piperno et al., "Characterization of a Protein that Regulates the DNA–binding Activiting of NF–AT, the Nuclear Factor of Activated T Cells", *Proc. Natl. Acad. Sci. USA*, vol. 88, pp. 11431–11434.

Jain et al., "The T–cell transcription factor $NFAT_p$ is a substract for calcineurin and interacts with Fos and Jun", *Nature*, vol. 365, pp. 352–355.

Li et al., "Cloning of a cellular factor, interleukin binding factor, that binds to NFAT–like motifs in the human immunodeficiency virus long terminal repeat", 1991, *Proc. Natl. Acad. Sci. USA*, vol. 88, pp. 7739–7743.

McCaffrey et al., "$NF–AT_p$, a T Lymphocyte DNA–binding Protein That Is a Target for Calcineurin and Immunosuppressive Drugs", 1993, *J. Biol. Chem.*, vol. 268, No. 5, pp. 3747–3752.

McCaffrey et al., "Isolation of the Cyclosporin–Sensitive T Cell Transcription Factor $NFAT_p$", 1993, Science, vol. 262, pp. 750–754.

Northrop et al., "Characterization of the Nuclear and Cytoplasmic Components of the Lymphoid–specific Nuclear Factor of Activated T Cells (NF–AT) Complex", 1993, *J. Biol. Chem.*, vol. 268, No. 4, pp. 2917–2923.

Thompson et al., "cis–Acting Sequences Required for Inducible Interleukin–2 Enhancer Function Bind a Novel Ets–Related Protein, Elf–1", 1992, *Mol. Cell Biol.*, vol. 12, No. 1, pp. 1043–1053.

O'Farrel et al., "High Resolution Two–Dimensional Electrophoresis of Basic as Well as Acidic Proteins", 1977, *Cell*, vol. 12, pp. 1133–1142.

Bradford, "A Rapid and Sensitive Method for the Quantitation of Microgram Quantities of Protein Utilizing the Principle of Protein–Dye Binnding", 1976, *Analy. Biochem.*, vol. 72, pp. 248–254.

Sanger, et al., "DNA Sequencing with Chain–Terminating Inhibitors", 1977, *Proc. Natl. Acad. Sci.*, vol. 74, pp. 5463–5467.

Laemmli, "Cleavage of Structural Proteins during the Assembly of the Head of Bacteriophage T4", 1970, *Nature*, vol. 227, pp. 680–685.

Hunkapiller et al., Meth. Enzymol. 91:227–236 (1983).

Lathe, J. Mol. Biol. 183:1–12 (1985).

Ohtsuka et al., J. Biol. Chem. 260:2605–2608 (1985).

Tokumitsu et al., Biochem. Biophys. Res. Comm. 196:737–744 (1993).

Northrop et al., Nature 369:497–502 (1994).

Untreated

CsA

Mixed

1
GSSASFISDTFSPYTSPCVSPNNAGPDDLCPQFQNIPAHYSPRTSPIMSP

51
RTSLAEDSCLGRHSPVPRPASRSSSPGAKRRHSCAEALVAPLPAASPQRS

101
RSPSPQPSPHVAPQDDSIPAGYPPTAGSAVLMDALNTLATDSPCGIPSKI

151
WKTSPDPTPVSTAPSKAGLARHIYPTVEFLGPCEQEERRNSAPESILLVP
x 23.3

201
PTWPKQLVPAIPICSIPVTASLPPLEWPLSNQSGSYELRIEVQPKPHHRA
72 x

251
HYETEGSRGAVKAPTGGHPVVQLHGYMENKPLGLQIFIGTADERILKPHA

301
FYQVHRITGKTVTTTSYEKIVGNTKVLEIPLEPKNNMRATIDCAGILKLR

351
NADIELRKGETDIGRKNTRVRLVFRVHVPEPSGRIVSLQAASNPIECSQR

401
SAHELPMVERQDMDSCLVYGGQQMILTGQNFTAESKVVFMEKTTDGQQIW
48 23.2

451
EMEATVDKDKSQPNMLFVEIPEYRNKHIRVPVKVNFYVINGKRKRSQPQH

501
FTYHPVPAIKTEPSDEYEPSLICSPAHGGLGSQPYYPQHPMLAESPSCLV

551
ATMAPCQQFRSGLSSPDARYQQSPAAALYQRSKSLSPGLLGYQQPSLLA
10.1 23.1

601
APLGLADAHRSVLVHAGSQGQGQGSTLRHTSSASQQASPVIHYSPTNQQL

651
RGGGHQEFQHIMYCENFGPSSARPGPPPINQGQRLSPGAYPTVIQQQTAP
25

701
SQRAAKNGPSDQKEALPTGVTVKQEQNLDQTYLDDAATSESWVGTERYIE

751
RKFWKKTLVQPGLLPSFLLLGSLSAGPRSQTPSERKPIEEDVPLSCSQIA

801
WCCQHPLGTCPVLPGPLAVEWWEGQLGRGLEPIPWAPDSAGSLHEVDSVG

851
LAGVVGMVLLTLMHHFSMDQNQTPSPHWQRHKEVASPGWI@ SEQ ID NO: 5

FIG. 10

| | | | | | |
|---|---|---|---|---|---|
| ---------- | GCATACCCCG | ATGATGTCCT | GGACTATGGC | CTCAAGCCAT | 40 |
| ACAGCCCCCT | TGCTAGTCTC | TCTGGCGAGC | CCCCCGGCCG | ATTCGGAGAG | |
| CCGGATAGGG | TAGGGCCGCA | GAAGTTTCTG | AGCGCGGCCA | AGCCAGCAGG | 140 |
| GGCCTCGGGC | CTGAGCCCTC | GGATCGAGAT | CACTCCGTCC | CACGAACTGA | |
| TCCAGGCAGT | GGGGCCCCTC | CGCATGAGAG | ACGCGGGCCT | CCTGGTGGAG | 240 |
| CAGCCCCCCC | TGGCCGGGGT | GGCCGCCAGC | CCGAGGTTCA | CCCTGCCCGT | |
| GCCCGGCTTC | GAGGGCTACC | GCCAGCCGCT | TTGCTTGAGC | CCCGCTAGCA | 340 |
| GCGGCTCCTC | TGCCAGCTTC | ATTTCTGACA | CCTTCTCCCC | CTACACCTGC | |
| CCCTGCGTCT | CGCCCAATAA | CGGCGGGCCC | GACGACCTGT | GTCCGCAGTT | 440 |
| TCAAAACATC | CCTGCTCATT | ATTCCCCCAG | AACCTCGCCA | ATAATGTCAC | |
| CTCGAACCAG | C-TCGCCGAG | GACAGCTGCC | TGGGCCGCCA | CTCGCCCGTG | 540 |
| CCCCGTCCGG | CCTCCCGCTC | CTCATCGCCT | GGTGCCAAGC | GGAGGCATTC | |
| GTGCGCCGAG | GCCTTGGTTG | CCCTGCCGCC | CGGAGCCTCA | CCCCAGCGCT | 640 |
| CCCGGAGCCC | CTCGCCGCAG | CCCTCATCTC | ACGTGGCACC | CCAGGACCAC | |
| GGCTCCCCGG | CTGGGTACCC | CCCTGTGGCT | GGCTCTGCCG | TGATCATGGA | 740 |
| TGCCCTGAAC | AGCCTCGCCA | CGGACTCGCC | TTGTGG-ATC | CCCCCCAAGA | |
| TGTGGAAGAC | CAGCCCTGAC | CCCTCGCCGG | TGTCTCGCGC | CCCATCCAAG | 840 |
| GC-GGCCTGC | CTCGCCACAT | CTACCCGGCC | GTGGAGTTCC | TGGGGC--TG | |
| CGAGCAGGGC | GAGAGGAGAA | ACTCGGCTCC | AGAATCCATC | CTGCTGGTTC | 940 |
| CGCCCACTTG | -CCCAAGCCG | CTGGTGCCTG | CCATTCCCAT | CTCGACGATC | |
| CCATGAGCTC | GATCCCTCCC | T-CACTTGAG | TGGCCGCTGT | CCAGTCAGTC | 1040 |
| ATCGCGTTAC | GAGCTGCGGA | TCGAGGTGCA | GC (SEQ ID NO:11) | | |

FIG. 17

...AYPDDVLDYGLKPYSPLASLSGEPPGRFGEPDRVGPQKFLSAAKPAG

ASGLSPRIEITPSHELIQAVGPLRMRDAGLLVEQPPLAGVAASPRFTLPV

PGFEGYRQPLCLSPASSGSSASFISDTFSPYTCPCVSPNNGGPDDLCPQF

QNIPAHYSPRTSPIMSPRTSLAEDSCLGRHSPVPRPASRSSSPGAKRRHS

CAEALVALPPGASPQRSRSPSPQPSSHVAPQDHGSPAGYPPVAGSAVIMD

ALNSLATDSPCGIPPKMWKTSPDPSPVSRAPSKAGLPRHIYPAVEFLGPC

EQGERRNSAPESILLVPPTWPKPLVPAIPISTIP*ARSLPPLEWPLSSQS

SRYELRIEVQ ... (SEQ ID NO:12)

FIG. 18

| | | | | | | |
|---|---|---|---|---|---|---|
| | | | | | | 50 |
| m | GCGGCTCCTC | TGCCAGCTTC | ATTTCTGACA | CCTTCTCCCC | CTACACCTCG | |
| h | ---------- | ---------- | ---------- | ---------- | --------GC | |
| | | | | | | 100 |
| m | CCCTGCGTCT | CACCCAATAA | CGCCGGGCCC | GACGACCTGT | GTCCCCAGTT | |
| h | ---------- | -G-------- | --G------- | ---------- | ----G----- | |
| | | | | | | 150 |
| m | TCAAAACATC | CCTGCTCATT | ATTCCCCCAG | AACCTCTCCA | ATAATGTCAC | |
| h | ---------- | ---------- | ---------- | ------G--- | ---------- | |
| | | | | | | 200 |
| m | CTCGAACCAG | CCTCGCCGAG | GACAGCTGCC | TGGGCCGACA | CTCGCCCGTG | |
| h | ---------- | -.-------- | ---------- | -------C-- | ---------- | |
| | | | | | | 250 |
| m | CCCCGTCCGG | CATCCCGCTC | CTCCTCACCC | GGTGCCAAGC | GGAGGCATTC | |
| h | ---------- | -C-------- | ---A--G--T | ---------- | ---------- | |
| | | | | | | 300 |
| m | GTGCGCAGAG | GCTTTGGTTG | CTCCTCTGCC | CGCAGCCTCA | CCCCAGCGCT | |
| h | ------C--- | --C------- | -C-TG-C--- | --G------- | ---------- | |
| | | | | | | 350 |
| m | CCCGGAGCCC | CTCGCCACAG | CCCTCGCCTC | ACGTGGCACC | GCAGGACGAC | |
| h | ---------- | -------G-- | -----AT--- | ---------- | C------C-- | |
| | | | | | | 400 |
| m | AGCATCCCCG | CTGGGTACCC | CCCCACGGCC | GGCTCTGCTG | TTCTCATGGA | |
| h | G--TC---G- | ---------- | ---TGT---T | --------C- | -GA------- | |
| | | | | | | 450 |
| m | TGCCCTCAAC | ACCCTGGCCA | CCGACTCGCC | CTGCGGGATC | CCCTCCAAGA | |
| h | ------G--- | -G---C---- | -G-------- | T--T--.--- | ---C------ | |
| | | | | | | 500 |
| m | TATGGAAGAC | CAGTCCTGAC | CCGACGCCTG | TGTCCACCGC | TCCGTCCAAG | |

FIG. 19A

```
h   -G--------   ---C------   --CT----G-   ----TCG---   C--A------

                                                               550
m   GCTGGCCTGG   CCCGCCACAT   CTACCCTACT   GTGGAGTTCC   TGGGGCCATG

h   --.------C   -T--------   ------GG-C   ----------   ------..--

                                                               600
m   TGAGCAGGAG   GAGAGGAGGA   ATTCCGCTCC   AGAGTCCATC   CTGCTGGTAC

h   C-------GC   --------A-   -C--G-----   ---A------   --------T-

                                                               650
m   CACCTACTTG   GCCCAAGCAG   TTGGTGCCGG   CCATTCCCAT   CTGCAGCATC

h   -G--C-----   .-------C-   C-------T-   ----------   --CG-CG---

                                                               700
m   CCTGTGACTG   CATCCCTCCC   ACCACTCGAG   TGGCCACTCT   CCAATCAGTC

h   --ATGAG--C   G---------   T.----T---   -----G--G-   ---G------

m   GGGCTCCTAT   GAGCTACGGA   TTGAGGTCCA   AC   (SEQ ID NO:8)

h   ATCGCGT--C   -----G----   -C-----G--   G-   (SEQ ID NO:21)
```

FIG. 19B 1 ggatgacgCA GCCACTTCAG AAAGCTGGGT TGGGACAGAA AGGTATATAG AGAGAAAATT ...
(SEQ ID NO:13)
2 ggatgacgAG TTGATAGACA CACACCTTAG CTGGATACAA AACATATTAT GA
(SEQ ID NO:14)
3 ggatgacgTT AATGAAATCA TCAGGAAGGA GTTTTCAGGA CCTCCCTCCC GAAATCAGAC CTAG
(SEQ ID NO:15)

The splice site is after the first nucleotide in the third codon shown.

gat gac gCA GCC ACT TCA GAA AGC TGG GTT GGG ACA GAA AGG TAT ATA ...

D D A A T S E S W V G T E R Y I ...
(SEQ ID NO:16)

gat gac gAG TTG ATA GAC ACA CAC CTT AGC TGG ATA CAA AAC ATA TTA TGA

D D E L I D T H L S W I Q N I L *
(SEQ ID NO:17)

gat gac gTT AAT GAA ATC ATC AGG AAG GAG TTT TCA GGA CCT CCC TCC CGA AAT CAG

D D V N E I I R K E F S G P P S R N Q

ACC TAG

T *
(SEQ ID NO:18)

FIG. 20

1 GCGGCTCCTC TGCCAGCTTC ATTTCTGACA CCTTCTCCCC CTACACCTCG
51 CCCTGCGTCT CACCCAATAA CGCCGGGCCC GACGACCTGT GTCCCCAGTT
101 TCAAAACATC CCTGCTCATT ATTCCCCCAG AACCTCTCCA ATAATGTCAC
151 CTCGAACCAG CCTCGCCGAG GACAGCTGCC TGGGCCGACA CTCGCCCGTG
201 CCCCGTCCGG CATCCCGCTC CTCCTCACCC GGTGCCAAGC GGAGGCATTC
251 GTGCGCAGAG GCTTTGGTTG CTCCTCTGCC CGCAGCCTCA CCCCAGCGCT
301 CCCGGAGCCC CTCGCCACAG CCCTCGCCTC ACGTGGCACC GCAGGACGAC
351 AGCATCCCCG CTGGGTACCC CCCCACGGCC GGCTCTGCTG TTCTCATGGA
401 TGCCCTCAAC ACCCTGGCCA CCGACTCGCC CTGCGGGATC CCCTCCAAGA
451 TATGGAAGAC CAGTCCTGAC CCGACGCCTG TGTCCACCGC TCCGTCCAAG
501 GCTGGCCTGG CCCGCCACAT CTACCCTACT GTGGAGTTCC TGGGGCCATG
551 TGAGCAGGAG GAGAGGAGGA ATTCCGCTCC AGAGTCCATC CTGCTGGTAC
601 CACCTACTTG GCCCAAGCAG TTGGTGCCGG CCATTCCCAT CTGCAGCATC
651 CCTGTGACTG CATCCCTCCC ACCACTCGAG TGGCCACTCT CCAATCAGTC
701 GGGCTCCTAT GAGCTACGGA TTGAGGTCCA ACCCAAGCCC CATCACCGGG
751 CCCACTATGA GACGGAGGGC AGCCGTGGCG CTGTCAAAGC CCCAACAGGA
801 GGACACCCTG TGGTGCAGCT CCACGGCTAC ATGGAGAACA AGCCTCTGGG
851 GCTTCAGATC TTCATTGGGA CAGCAGATGA GAGGATCCTT AAGCCGCACG
901 CCTTCTACCA AGTACACAGG ATCACTGGGA AAACGGTCAC CACCACGAGC
951 TATGAGAAGA TCGTAGGCAA CACCAAGGTC CTGGAGATCC CCCTGGAGCC
1001 AAAGAACAAC ATGAGAGCCA CCATCGACTG TGCAGGCATC CTGAAGCTCC
1051 GAAACGCTGA CATCGAGCTG CGGAAGGGCG AGACGGACAT CGGCAGGAAG
1101 AACACGCGTG TGCGCCTGGT GTTCCGCGTG CACGTCCCAG AGCCCAGTGG
1151 GCGCATCGTC TCCCTGCAGG CTGCGTCCAA CCCCATCGAG TGCTCTCAGC
1201 GCTCTGCCCA CGAGCTGCCC ATGGTGGAGA GACAAGACAT GGACAGCTGC
1251 CTGGTCTACG GGGGCCAGCA GATGATCCTC ACGGGCCAGA ACTTCACAGC
1301 GGAGTCCAAG GTTGTGTTCA TGGAGAAGAC TACAGATGGG CAGCAGATTT

FIG. 21A

1351 GGGAGATGGA AGCTACGGTG GATAAAGACA AGAGCCAGCC TAACATGCTT
1401 TTTGTTGAGA TCCCCGAGTA TCGGAACAAG CACATCCGCG TGCCCGTGAA
1451 AGTCAACTTC TACGTCATCA ACGGAAAGAG GAAACGAAGT CAGCCACAGC
1501 ACTTTACCTA CCACCCAGTC CCTGCCATCA AGACAGAGCC CAGCGATGAG
1551 TATGAACCAT CTTTGATCTG CAGCCCCGCC CATGGAGGCC TGGGGAGCCA
1601 GCCATATTAC CCACAGCACC CAATGCTGGC CGAGTCCCCC TCCTGCCTTG
1651 TGGCTACCAT GGCCCCCTGC CAACAGTTCC GCTCGGGGCT CTCATCCCCC
1701 GATGCTCGCT ACCAACAGCA GAGCCCCGCA GCTGCCCTCT ACCAGAGAAG
1751 CAAGAGCCTG AGTCCCGGCC TGCTGGGCTA CCAGCAGCCG TCCCTCCTGG
1801 CAGCACCCTT GGGTCTGGCT GATGCCCACC GCTCTGTGCT GGTGCATGCT
1851 GGTTCTCAGG GGCAGGGGCA GGGCTCCACC CTCCGACACA CATCCTCGGC
1901 CAGCCAGCAG GCCTCACCCG TGATCCACTA CTCACCCACC AACCAGCAGC
1951 TTCGCGGTGG GGGTCACCAG GAGTTCCAGC ATATCATGTA CTGTGAAAAC
2001 TTCGGCCCCA GCTCTGCCAG GCCTGGCCCG CCTCCCATCA ACCAAGGTCA
2051 GAGGCTGAGC CCGGGCGCCT ACCCCACAGT CATCCAACAA CAGACTGCCC
2101 CGAGCCAAAG AGCTGCCAAA AACGGACCCA GTGACCAGAA GGAAGCTCTG
2151 CCCACGGGAG TGACCGTCAA ACAGGAACAG AACCTGGACC AGACCTACCT
2201 GGATGACGCA GCCACTTCAG AAAGCTGGGT TGGGACAGAA AGGTATATAG
2251 AGAGAAAATT TTGGAAGAAG ACCCTTGTGC AGCCTGGGCT CCTGCCCTCA
2301 TTTTTACTTC TTGGCTCCCT GTCTGCTGGA CCAAGGTCAC AGACACCATC
2351 AGAAAGAAAG CCCATAGAGG AAGACGTGCC CTTGAGTTGC AGCCAGATAG
2401 CCTGGTGTTG TCAGCATCCC TTGGGGACCT GCCCTGTCCT GCCAGGGCCT
2451 TTAGCTGTAG AGTGGTGGGA AGGGCAGCTC GGGCGTGGGC TGGAGCCAAT
2501 TCCCTGGGCT CCAGACAGTG CCGGCAGCCT CCATGAGGTG GACAGTGTAG
2551 GCCTGGCGGG AGTGGTCGGA ATGGTTCTGC TCACTCTTAT GCACCACTTC
2601 TCCATGGATC AGAACCAGAC CCCCTCTCCT CACTGGCAAA GGCACAAAGA
2651 GGTTGCTAGC CCAGGCTGGA TCTGA (SEQ ID NO:20)

FIG. 21B

```
ATGGGCTCAT  CAACTTCATC  AAGCAGCAGC  GCGAGGCCAG  AGTCCAATAA—50
ACTCGTGCTC  ATCTGCAGCC  TCCTCTGTGA  CTCCCCTTCT  CTTCTCGTCC—100
CTCCTCCCCG  GAGC  (SEQ ID NO: 19)                        —114
```

FIG. 22

NF-$AT_p$, A T LYMPHOCYTE DNA-BINDING PROTEIN

STATEMENT OF RELATED APPLICATION

This application is a continuation-in-part of U.S. patent application Ser. No. 08/017,052 which was filed on Feb. 11, 1993, now abandoned, which in turn is a continuation-in-part of U.S. Ser. No. 08/006,067 filed on Jan. 15, 1993, now abandoned.

STATEMENT AS TO FEDERALLY SPONSORED RESEARCH

This work was supported by National Institutes of Health Grants CA42471 and GM46227. The U.S. Government therefore has certain rights to this invention.

FIELD OF THE INVENTION

The invention relates to immunosuppressant compounds.

BACKGROUND OF THE INVENTION

The nuclear factor of activated T cells (NF-AT) is an inducible, lymphoid-specific transcription factor that is essential for expression of the IL-2 gene upon T cell activation (For a review, see Ullman, K. S., Northrop, J. P., Verweij, C. L., Crabtree, G. R. (1990) *Ann. Rev. Immunol.* 8, 421–452). By cell fractionation and reconstitution experiments, NF-AT was shown to be assembled in the nucleus of activated T cells from a T cell-specific component that is preexisting before activation and an inducible nuclear component (Flanagan, W. M., Corthesy, B., Bram, R. J., and Crabtree, G. R. (1991) *Nature* 352, 803–807). The preexisting component of NF-AT (here designated NF-$AT_p$) was subsequently identified in hypotonic extracts of unstimulated T cells by its ability to bind specifically to an oligonucleotide corresponding to the distal NF-AT sequence from the murine IL-2 gene promoter (Jain, J., McCaffrey, P. G., Valge-Archer, V. E., and Rao, A. (1992) *Nature* 356, 801–804). In addition, it was shown that the inducible nuclear component of NF-AT consists of Fos and Jun proteins, (Jain et al., supra).

Assembly of NF-AT in the nucleus requires two intracellular signals, the activation of protein kinase C and an increase in cytosolic free calcium, both of which are provided by activation of T cells through the T cell antigen receptor. Activation of protein kinase C is necessary for transcriptional induction of Fos and Jun genes (Jain, J., Valge-Archer, V. E., and Rao, A. (1992) *J. Immunol.* 148, 1240–1250). An increase in intracellular calcium is necessary for the appearance of NF-$AT_p$ in the nucleus, presumably reflecting its translocation from the cytosol (Flanagan, W. M., Corthesy, B., Bram, R. J., and Crabtree, G. R. (1991) *Nature* 352, 803–807). The immunosuppressive drugs cyclosporin A (CsA) and FK506 block induction of NF-AT by interfering with the calcium-dependent appearance of NF-$AT_p$ in the nucleus. CsA and FK506, when complexed with their specific intracellular binding proteins (cyclophilin and FK506 binding protein, respectively), potently inhibit the activity of the calcium- and calmodulin-dependent phosphatase, calcineurin (Klee, C. B., Draetta, G. F., Hubbard, M. J. (1987) *Adv. Enz.* 61, 149–200); Fruman, D. A., Klee, C. B., Bierer, B. E., Burakoff, S. J. (1992) *Proc. Natl. Acad. Sci. USA* 89, 3686–3690), towards peptide substrates (Liu, J., Farmer, J. D., Jr., Lane, W. S., Friedman, J., Weissman, I., and Schreiber, S. L. (1991) *Cell* 66, 807–815) Based on these results, it has been proposed that NF-$AT_p$ in the cytosol may be a target for calcineurin, either directly as a substrate or indirectly via a phosphatase cascade (Schreiber, S. L., and Crabtree, G. R. (1992) *Immunology Today* 13, 136–142).

SUMMARY OF THE INVENTION

In accordance with the present invention, we have demonstrated that the DNA-binding component of the NF-AT T cell nuclear factor, herein referred to as NF-$AT_p$, is a 90–140 kDa T cell phosphoprotein that binds directly and specifically to the NF-AT sequence and that calcineurin can cause dephosphorylation of this protein in T cell lysates. These findings directly implicate NF-$AT_p$ in the chain of events by which CsA and FK506 inhibit IL-2 gene induction.

As described in detail below, NF-$AT_p$ is present in resting T cells predominantly in a form migrating with an apparent molecular weight of 110–140 kDa, while NF-$AT_p$ from nuclear extracts of activated T cells migrates with a lower apparent molecular weight (90–125 kDa). This difference reflects dephosphorylation of NF-$AT_p$, since treatment of NF-$AT_p$ with calf intestinal phosphatase or the calcium- and calmodulin-dependent phosphatase calcineurin in vitro results in a similar decrease in its apparent molecular weight. We show that NF-$AT_p$ is dephosphorylated in cell lysates by a calcium-dependent process that is blocked by inclusion of EGTA or a specific peptide inhibitor of calcineurin in the cell lysis buffer. Moreover, dephosphorylation of NF-$AT_p$ in cell extracts is inhibited by prior treatment of T cells with the immunosuppressive drugs cyclosporin A (CsA) or FK506, which inhibit the phosphatase activity of calcineurin when complexed with their specific binding proteins, cyclophilin and FK506 binding protein. This work identifies NF-$AT_p$ as a DNA-binding phosphoprotein and a target for drug/immunophilin/calcineurin complexes thought to mediate the inhibition of IL-2 gene induction by CsA and FK506.

In one embodiment, the invention provides a purified preparation of NF-$AT_p$ protein, preferably a human NF-$AT_p$ protein. The protein can be phosphorylated, or not phosphorylated. In accordance with the invention, purified preparations of NF-$AT_p$ protein can be complexed with a Fos protein, a Jun protein, or with both a Fos and a Jun protein to form a complex resembling the native nuclear factor of activated T cells (NF-AT), which can be used to screen for regulatory sequences in the promoter regions of other cytokine genes or genes of other immune regulatory proteins for binding to the complexes. Such genes encode proteins that may constitute a family whose transcription is regulated by a similar mechanism and provide the basis of drug design strategies to manipulate the immune response.

In another embodiment of the invention, there is provided an isolated DNA encoding NF-$AT_p$. The DNA preferably encodes a mammalian NF-$AT_p$ protein or functional fragment, derivative, or isoform thereof, and most preferably encodes a human or a murine NF-$AT_p$ protein. The isolated DNA may encode a protein which contains the amino acid sequence of murine NF-$AT_p$ (SEQ ID NO:5) or human NF-$AT_p$ (SEQ ID NO:12). The invention also includes isolated DNA containing part or all of either the sequence of murine NF-$AT_p$ shown in FIG. 21 (SEQ ID NO:20) or human NF-$AT_p$ shown in FIG. 17 (SEQ ID NO:11), or FIG. 22 (SEQ ID NO:19). Also provided are vectors containing the isolated DNA; cells, which can be prokaryotic or eukaryotic, containing the isolated DNA; and methods of manufacturing NF-$AT_p$. The methods comprise culturing the cells containing NF-$AT_p$ under conditions permitting expression of the DNA.

In yet another embodiment of the invention, there are provided antibodies or fragments or variants thereof that bind to an epitope of the NF-$AT_p$ protein. The antibodies can be polyclonal or monoclonal, and can recognize an epitope of the NF-$AT_p$ protein in a denatured or native form. The antibodies, especially the antibodies that bind to an epitope of native NF-$AT_p$ protein, are particularly useful in detecting expression of NF-$AT_p$ in a cell. Expression of the NF-$AT_p$ protein can be detected by contacting a mixture of proteins from the cells of interest with an anti-NF-$AT_p$ antibody of the invention, which is labeled, and detecting immune complex formation.

Expression of the NF-$AT_p$ protein in a cell can also be detected by contacting mRNA obtained from the cell with a labeled hybridization probe comprising, for example, a single-stranded segment of isolated DNA encoding a fragment of the NF-$AT_p$ protein and detecting hybridization of the probe with the mRNA. The invention includes an isolated DNA containing 20 nucleotides that hybridizes under stringent conditions to a strand of a DNA encoding NF-$AT_p$. By the term "stringent conditions" is meant DNA hybridization and wash conditions characterized by relatively high temperature and low salt concentration, e.g., conditions described in Sambrook et al., (1989) *Molecular Cloning: a Laboratory Manual*, second edition., Cold Spring Harbor Press, Cold Spring Harbor, N.Y), page 7.52 of which is herein incorporated by reference. The segment of DNA may be 20 nucleotides, preferably 50 nucleotides, more preferably 100 nucleotides, and most preferably 200 nucleotides in length.

In yet another embodiment, the invention includes an isolated DNA which encodes a segment of NF-$AT_p$ which binds to Fos-Jun or Jun—Jun, e.g., nucleotides 672–2063 of SEQ ID:20. By "Fos-Jun" is meant the heterodimeric complex of the transcription factors Fos and Jun. By "Jun—Jun" is meant the homodimeric complex of the transcription factor, Jun.

Other embodiments of the invention are directed to methods for screening for potential immunosuppressant compounds, which interfere with or inhibit lymphokine gene activation through the NF-AT pathway. One such method takes advantage of our discovery that the NF-$AT_p$ exists in a phosphorylated form in inactivated T cells, but is dephosphorylated via a phosphatase after activation through the T cell receptor. This method involves providing purified, phosphorylated NF-$AT_p$ protein; contacting the NF-$AT_p$ protein with a phosphatase, such as calcineurin or calf intestinal phosphatase, in the presence of a candidate immunosuppressive compound; and determining whether dephosphorylation of NF-$AT_p$ by the phosphatase is inhibited by the candidate compound.

Another method for screening potential immunosuppressive agents in accordance with the present invention comprises providing purified NF-$AT_p$; contacting the purified NF-$AT_p$, in the presence of a candidate immunosuppressive compound, with an oligonucleotide comprising a sequence substantially identical to a 5' NF-AT DNA sequence which binds the NF-$AT_p$ component of the NF-AT complex and determining whether the candidate compound inhibits binding of the oligonucleotide. to NF-$AT_p$. In a preferred embodiment, the oligonucleotide is GCCCAAAGAGGAAAATTTGTTTCATACAG (SEQ ID NO:1).

Yet another method for screening potential immunosuppressive agents in accordance with the present invention involves providing purified NF-$AT_p$; contacting the NF-$AT_p$ with a Fos protein in the presence of a candidate immunosuppressive compound; and determining whether the candidate compound inhibits binding of the Fos protein to the NF-$AT_p$ protein. The same method can alternatively be used with a Jun protein or a combination of Fos and Jun proteins, and involves providing purified NF-$AT_p$; contacting the NF-$AT_p$ with Jun or a combination of Fos and Jun in the presence of a candidate immunosuppressive compound; and determining whether the candidate compound inhibits binding of the proteins to the NF-$AT_p$ protein.

Other aspects of the invention will be appreciated by persons skilled in the art from the specification and claims herein.

BRIEF DESCRIPTION OF THE DRAWING

In FIG. 2A, Ar-5 cells were untreated (M), or treated for 2 hours with cross-linked anti-CD3ε antibody (αCD3), 1 μM CsA, or both anti-CD3ε and CsA as indicated. Nuclear extracts were prepared and 200 μg of total protein was fractionated by SDS-PAGE, followed by elution and renaturation of proteins as in FIG. 1. The binding of proteins from three consecutive gel slices (representing the molecular weight ranges 122–144, 102–122, and 86–102 kDa as indicated) to the NF-AT oligonucleotide is shown. In FIG. 1B, specificity of binding of the renatured proteins to the NF-AT oligonucleotide. Renatured NF-AT-binding proteins from hypotonic extracts (left panel) or nuclear extracts (right panel) were assayed for binding to the NF-AT oligonucleotide in the presence of a 200-fold excess of unlabeled NF-AT oligonucleotide (here labeled NF-AT-1, lane 2), or oligonucleotides bearing mutations in the NF-AT sequence (M1, M2, M3, lanes 3–5).

In FIG. 5C, equal amounts of extracts (125 μg protein each) from untreated or CsA-treated cells were mixed after boiling in SDS-PAGE sample buffer and fractionated as for FIGS. 5A and 5B. In each of FIGS. 5A through 5C, the solid arrow denotes NF-$AT_p$, while the open arrow denotes a minor complex appearing in slice 3 (see text for discussion).

FIG. 10 is a diagram of the deduced amino acid sequence of murine NF-$AT_p$ (SEQ ID NO:5) in which the sequences of tryptic peptides from purified NF-$AT_p$ are underlined. "X" in the underlining for peptides 23.3 and 72 indicate positions at which the identity of the amino acid could not be determined unambiguously. The sequence between the arrowheads represents the NF-$AT_p$ sequence contained within the recombinant protein that was expressed in bacteria.

FIG. 17 is a representation of a partial cDNA sequence of human NF-$AT_p$ (SEQ ID NO:11).

FIG. 18 is a representation of the amino acid sequence deduced from the partial cDNA sequence of human NF-$AT_p$ (SEQ ID NO:12).

FIG. 19 is a diagram showing the comparison of the murine and human cDNA sequences in the region of overlap encoding NF-$AT_p$ (SEQ ID NO:8 and SEQ ID NO:21, respectively).

FIG. 20 is a diagram showing murine isoforms of NF-$AT_p$. Sequences shown are (1) nucleotides 2201–2260 of mNF-$AT_p$Q1B1/A sequence, (2) splicing variant mNF-$AT_p$-R3B1, and (3) splicing variant mNF-$AT_p$-T2B1. The alternatively spliced forms are identical in sequence to mNF-$AT_p$Q1B1/A in the region up to and including nucleotide 2208 of mNF-$AT_p$Q1B1/A, shown in lower case letters. While the coding sequence of NF-$AT_p$-Q1B1/A continues 3' to the 60-nucleotide region shown, both variant forms have in-frame stop codons, shown in boldface type.

FIG. 21 is a partial cDNA sequence of murine and NF-$AT_p$ (SEQ ID NO:20) (GenBank U02079) from the plasmid mNFATp-Q1B1/A. The plasmid mNFATp-Q1B1/A also contains ~150 nucleotides of 3'-untranslated region after the stop codon.

FIG. 22 is a partial cDNA sequence from the human NF-$AT_p$ gene (SEQ ID NO:19).

DETAILED DESCRIPTION

Purification of NF-$AT_p$

Figure 1:
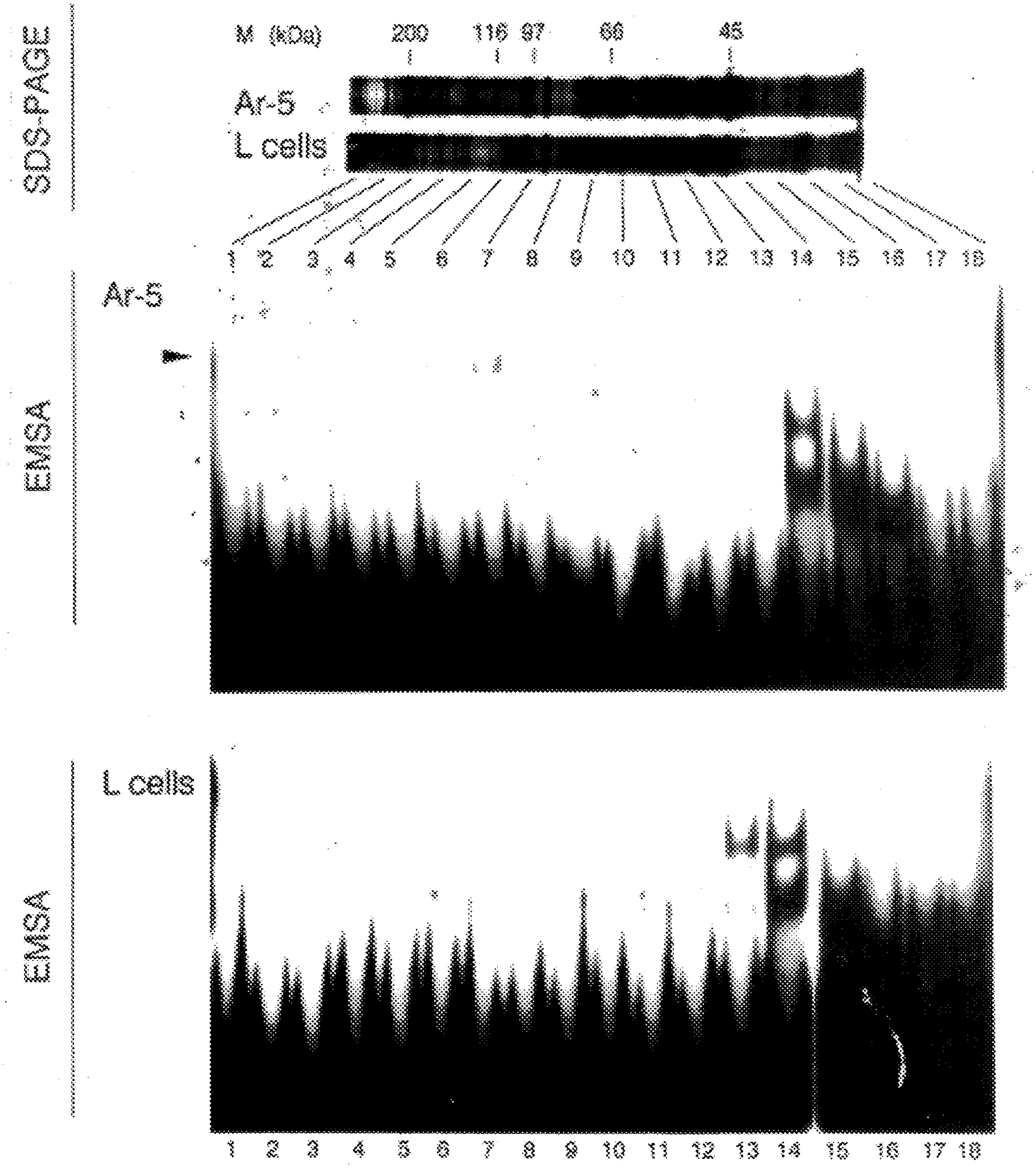
FIG. 1 is a series of photographs of sodium dodecyl sulfate-polyacrylamide gel electrophoresis (SDS-PAGE) gels showing the identification of T cell-specific NF-AT-binding proteins by renaturation of denatured protein separated and purified from SDS-PAGE gels. The top portion of the figure is a silver stain of an analytical 10% SDS-PAGE gel after fractionation of hypotonic extracts (4 μg total protein) from the murine T cell clone Ar-5 or a murine fibroblast cell line (L cells). The migration of standards and their molecular weights in kDa are indicated above. The bottom portions of the figure illustrate DNA-binding activity of proteins eluted and renatured from a preparative SDS-polyacrylamide gel, and assayed by electrophoretic mobility shift assay (EMSA) using an NF-AT oligonucleotide corresponding to the distal NF-AT site from the murine IL-2 promoter. Lanes 1–18 represent proteins eluted from successive 0.5 cm slices of a preparative SDS gel which was loaded with 200 μg total protein from the same extracts shown on the silver stained analytical gel. The arrow indicates the mobility of a protein-DNA complex detected in T cell extracts but not in L cell extracts. Lanes 6 and 7 contain proteins of apparent molecular weight 107–120 kDa and 93–107 kDa, respectively.

In one embodiment, the invention features a purified preparation of NF-$AT_p$ protein, which NF-$AT_p$ may be human, murine, bovine, or any other mammalian NF-$AT_p$, and which may be prepared, for example, from a natural source, from an expression system expressing an isolated DNA encoding NF-$AT_p$, or by synthetic means well known to persons skilled in the art. For example, the protein can be fractionated on a gel by SDS-PAGE, recovered, and then renatured, as described in the Examples.

A preferred method for purifying the NF-$AT_p$ involves lysing T cells that are rich sources of NF-$AT_p$ protein, precipitating the protein from cell lysates using a salt, such as ammonium sulfate, and purifying the NF-$AT_p$ protein on heparin-agarose and then on an affinity column.

The mouse T cell line Cl.7W2 (Valge-Archer et al., J. Immunol., 145:4355 (1990) has been found to be a rich source of NF-$AT_p$ protein, which can be used in the purification methods of the invention. Hypotonic extracts of the cells are prepared from these cells by lysing about $2.5\times10^7$ cells/ml in a buffer containing 10 mMTris (pH 8.0), 50 mM NaCl, 0.05% NP-40, 1 mM EDTA, 100 μg/ml aprotinin, 25 μM leupeptin, 2 mM PMSF, 10 mM iodoacetamide (IAM). The resulting extracts are centrifuged at low speed to remove the nuclei, then at 100,000 X g for one hour.

After centrifugation, the protein mixture is salt precipitated with an equal volume of appropriate reagent, which is preferably ammonium sulfate (final 1.5 M) and the precipitate resuspended in one-tenth volume relative to cell lysate of buffer, for example buffer A (20 mM Hepes, pH 7.4, 100 mM NaCl, 2 mM EDTA, 10% glycerol) containing 100 μg aprotinin, 25 μg leupeptin, 2 mM PMSF, and 10 mM IAM. The lysate is dialyzed versus the buffer A with 0.5 mM DTT.

The dialyzed extract is further purified by fractionation on heparin-agarose, in accordance with standard procedures. For example, a salt, such as NaCl, is added to the final concentration of lysate and the batch adsorbed onto heparin-agarose. The column is then loaded, washed with buffer (e.g. buffer A containing 0.2 M NaCl) and the proteins eluted with salt gradients of 0.2 to 1 M of reagent. Active fractions are pooled and dialyzed versus buffer. The recoveries at this step are typically 25 to 40%.

The material eluted from the heparin-agarose column is then subjected to two or three rounds of affinity purification using NF-AT oligonucleotides from the promoter region of a mammalian IL-2 gene. A sepharose column conjugated with about 100–200 nM multimerized murine NF-AT oligonucleotides, e.g. as in SEQ ID NO:1 per ml of resin can be used. In a typical purification, after two rounds of affinity chromatography, the specific activity of the NF-$AT_p$ preparation is about 160,000 U/mg of protein, indicating that about 2% of the protein recovered from the column was NF-$AT_p$.

Higher capacity columns for affinity purification can also be used, in which higher concentrations of NF-AT oligonucleotides are conjugated to the sepharose column. A high capacity column for affinity purification of sequence-specific DNA binding proteins that can be used in accordance with the invention is described in Larson and Verdine, *Nucleic Acids Research*, 20:3525 (1992). This column is used in the presence of herring sperm DNA.

The purified protein can be phosphorylated or unphosphorylated, and can be detected on a gel based upon the molecular weights determined in accordance with the present invention. Thus, the phosphorylated form of native NF-$AT_p$ exhibits a molecular weight about 110–140 kDa, while the dephosphorylated native protein exhibits a molecular weight of about 100–120 kDa.

The invention also includes purified preparations of a complex of NF-$AT_p$ with a Fos protein, a Jun protein, a combination of Fos plus Jun, or any other such protein with which NF-$AT_p$ is naturally functionally associated in vivo. It is contemplated that a number of members of the Fos and Jun protein families known to persons skilled in the art will bind NF-$AT_p$ and can therefore be used to form the complexes of the invention. c-Fos and c-Jun proteins are particularly suitable. See, Jain et al., (1992), supra. Other proteins that might be complexed with NF-$AT_p$ include other leucine zipper proteins, such as C/EPBs and CREBs. Like Fos and Jun, these proteins are capable of forming homodimers and heterodimers with one another and therefore might associate with NF-$AT_p$ in the same manner as Fos and Jun proteins.

The multicomponent complexes can be used in vitro transcription assays in order to identify other genes under the control of a promoter which responds to the same or structurally similar complex. An in vitro transcription assay that can be used in accordance with the invention is described, for example, in Kretzschmar et al., *Genes and Development,* 6:761–772 (1992), the pertinent portions of which are hereby incorporated by reference. The complexes are also useful in identifying candidate immunosuppressants which exhibit the ability to inhibit formation or to cause dissociation of the two or three component complex.

Isolation of DNA clones for NF-$AT_p$ and related proteins

Also within the invention are isolated DNAs which encode NF-$AT_p$. By "isolated DNA" is meant that the DNA molecule encodes NF-$AT_p$, but is free of the genes that, in the naturally-occurring genome of the organism from which the DNA of the invention is derived, immediately flank the gene encoding NF-$AT_p$. The term therefore encompasses, for example, a cDNA or a genomic DNA fragment produced by PCR or restriction endonuclease treatment, whether such cDNA or genomic DNA fragment is incorporated into a vector, integrated into the genome of the same or a different species than the organism from which it was originally derived, linked to an additional coding sequence to form a hybrid gene encoding a chimeric polypeptide, or independent of any other DNA sequences.

The DNA may be double-stranded or single-stranded, sense or antisense. The isolated DNA of the invention may be under the transcriptional control of a heterologous promoter (i.e., a promoter other than one naturally associated with the NF-$AT_p$ gene), which promoter, for example, may direct the expression of the DNA of the invention in a particular tissue or at a particular stage of development. A cell which contains such isolated DNA may be cultured under conditions permitting the expression of the DNA, providing a method for conveniently manufacturing recombinant NF-$AT_p$. Prokarytic or eukarotic cells can be used to express the protein encoded by the NF-$AT_p$ gene, including bacteria such as *E. coli*, yeast, insect cells, and mammalian cells such as CHO and COS cell lines well known to persons skilled in the art.

Fragments of the cDNA encoding NF-$AT_p$, e.g., fragments encoding functional domains, can be used to express protein to determine the 3-dimensional structure of the NF-$AT_p$ transcriptional regulatory complex. For example, the use of such fragments in competition assays may be useful in determining the regions of NF-$AT_p$ contacted by the Fos and Jun proteins.

By the term "isoform" is meant the product of alternative splicing of the nucleic acid transcript encoding NF-$AT_p$.

Antibodies That Bind To NF-$AT_p$

Purified NF-$AT_p$, or a peptide fragment thereof, may be used to generate by standard methods a monoclonal or polyclonal antibody capable of binding to NF-$AT_p$. In one preferred embodiment, a monoclonal antibody is generated, using the purified NF-$AT_p$ protein to immunize an appropriate laboratory animal, such as a mouse. The mouse can be, for example, an RBF/DnJ hyperimmune mouse (Jackson Laboratories, Bar Harbor, Me.). Three days after the final boost with protein, spleens are removed and spleen cells fused with NSI nonsecreting myeloma cells using standard protocols. Hybrid cells are selected by growth in medium containing HAT or hypoxanthine and azaserine. Hybridoma cells secreting antibodies to NF-$AT_p$ are identified by the ability of their culture supernatants to: (1) "supershift" or disrupt the NF-$AT_p$-DNA complex in a gel shift assay; and (2) stain the approximately 120 kd NF-$AT_p$ protein in a Western blot procedure. Hybrid cells the supernatants of which are positive in either assay are subcloned by limiting dilution, and used to produce ascites in (RBF/Dn×BALB/c) F1 mice.

In another preferred embodiment, polyclonal antisera are generated using NF-$AT_p$ peptides as immunogens in rabbits. For generation of antisera against proteolytic fragments of NF-$AT_p$, rabbits were immunized with synthetic peptides. For example, to generate peptide 72-specific antibodies, rabbits were immunized with a 21-amino-acid synthetic peptide contained within the amino acid sequence of peptide 72 conjugated to the carrier protein KLH.

The monoclonal antibodies generated by this procedure can be used to verify the identity of recombinant NF-$AT_p$ cDNA clones obtained by expression or in vitro transcription/translation of the NF-$AT_p$ cDNA clones. Polyclonal antisera can also be raised against the expressed recombinant NF-$AT_p$ protein. The antibodies are useful for determining the intracellular location of NF-$AT_p$: for example, by immunohistochemical staining of fixed and permeabilized T cells which are left unstimulated or are stimulated for 5 minutes to two hours with anti-CD3 antibody.

Such antibodies, or fragments thereof, which bind to an epitope of NF-$AT_p$ are also useful in a method for detecting expression of NF-$AT_p$ in a cell or a tissue, which method includes the steps of contacting proteins of the cell or tissue (e.g., using whole-cell lysates, proteins extracted from the cytoplasm or nucleus of the cell, or in situ on a tissue sample) with the antibody, and detecting immune complex formation using standard immunoassay techniques such as ELISA.

Likewise, a standard Northern blot assay employing a NF-$AT_p$ cDNA hybridization probe [e.g. full-length, single-stranded cDNA or a cDNA fragment at least 20 nucleotides in length (preferably at least 50 and more preferably at least 100) from a portion of the cDNA which is not homologous to any known cDNA sequence] can be used to ascertain the relative amount of NF-$AT_p$ mRNA in a cell or a tissue, in accordance with conventional techniques.

Either method of determining NF-$AT_p$ expression could be used to identify cells or tissues in which the level of NF-$AT_p$ expression was higher or lower than normal, and thus to diagnose certain disease conditions. For example, a rare form of inherited immune dysfunction has been attributed to a lack of functional NF-$AT_p$ in the T cells of the patient, while certain cancers and lymphomas are believed to involve overexpression of the NF-$AT_p$ gene.

Screening Methods

The characteristics of purified NF-$AT_p$ disclosed herein form the basis for several different methods for screening potential immunosuppressive agents. As an initial screen for potential immunosuppressants, candidate compounds can take the form of commercially available proteins or peptides (which are available in libraries from a variety of sources known and available to the skilled artisan), or organic or inorganic compounds, also available in libraries, that bind to the NF-$AT_p$ protein in either its phosphorylated or unphosphorylated form. Candidate compounds that bind to NF-$AT_p$ (as determined, for example, in an EMSA) can then be used in a more detailed screen, as described hereinafter.

For example, a candidate compound can be screened for its ability to inhibit dephosphorylation of NF-$AT_p$, which in turn should result in down regulation of the lymphokine gene and hence act as an immunosuppressant. Potential immunosuppressive agents which act by blocking the dephosphorylation of NF-$AT_p$ can be identified using any suitable phosphatase that exhibits the ability to dephosphorylate NF-$AT_p$, as described in the Examples herein. Preferred phosphatases include the calcium and calmodulin-dependent phosphatase calcineurin and other T cell phosphatases known to persons skilled in the art. The screen involves providing purified, phosphorylated NF-$AT_p$; contacting the NF-$AT_p$ with a T cell phosphatase, e.g., calcineurin, in the presence of a candidate immunosuppressive compound; and determining whether dephosphorylation of NF-$AT_p$ by the phosphatase is inhibited by the candidate compound. Phosphorylation status of NF-$AT_p$ can be assessed, for example, as described in Fruman et al., *Proc. Natl. Acad. Sci., USA,* 89:3686–3690 (May 1992), the pertinent portions of which are hereby incorporated by reference. See, especially page 3687 of Fruman et al. Alternatively, phosphorylation status of NF-AT can be evaluated using SDS-PAGE, as described in the Examples.

In another screening assay, purified NF-$AT_p$ is contacted, in the presence of the candidate immunosuppressive compound, with an oligonucleotide containing a sequence substantially identical to a mammalian NF-AT nucleotide sequence, preferably a sequence including GCCCAAAGAGGAAAATTTGTTTCATACAG (SEQ ID NO:1); and inhibition of binding of the oligonucleotide to NF-$AT_p$ by the candidate compound is ascertained, with an inhibition of binding being an indication that the candidate compound is a potential immunosuppressive agent.

Figure 7:
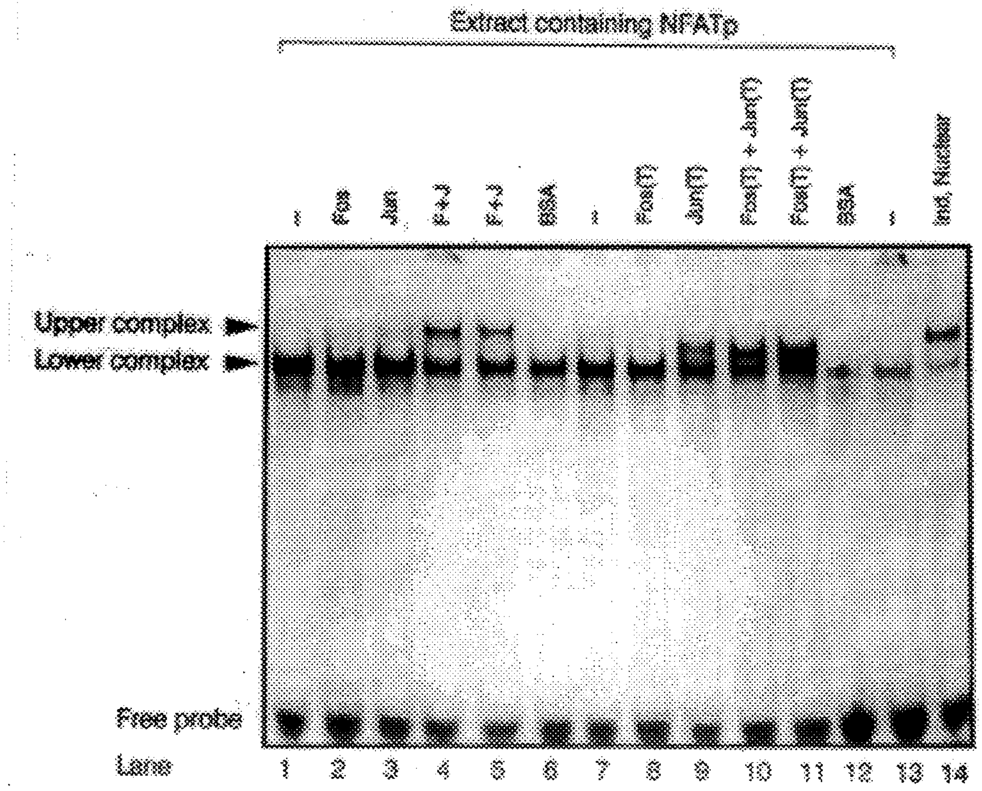
FIG. 7 is a photograph of an EMSA gel showing the results of an EMSA. Purified NF-$AT_p$ was shown to associate in vitro with recombinant Fos and Jun proteins. Partially purified NF-$AT_p$ was incubated with labeled oligonucleotide corresponding to the distal NF-AT site of the murine IL-2 promoter, either alone (lanes 1, 7, 13), with full length or truncated (T) recombinantly produced c-Fos and c-Jun proteins (lanes 2–5 and 8–11, respectively) or with an equivalent concentration of bovine serum albumin. Lane 5 contained 50% more c-Fos and c-Jun compared to lane 4. Lanes 11–13 contain half the amount of NF-$AT_p$ compared to lanes 1–10. Lane 14 shows a binding reaction of nuclear extracts from stimulated AR-5 T cells. Bound complexes were separated from free probe by EMSA. The position of free probe, of the lower (NF-$AT_p$) complex and upper (NF-$AT_p$-Fos-Jun) complex are indicated.

Other screening assays in accordance with the invention are designed to detect inhibition of binding of a Fos and/or Jun protein to NF-$AT_p$ by a candidate immunosuppressive compound. Such assays can be conducted in the presence or absence of NF-AT DNA. For example, in a DNA-based assay, incubation of purified or partially purified NF-$AT_p$ with labeled murine NF-AT site (SEQ ID NO:1) yields a single DNA-protein complex (See FIG. 7, lanes 1, 7, and 13) corresponding in migration to a "lower" NF-$AT_p$ complex (FIG. 7, lane 14). Inclusion of c-Fos and c-Jun proteins in the binding reaction mixture results in the appearance of a second complex (FIG. 7, lanes 4 and 5) whose migration is identical to that of the "upper" NF-$AT_p$/Fos/Jun nuclear complex (FIG. 7, lane 14). The complex is not observed when NF-$AT_p$ is incubated with c-Fos (See FIG. 7, lanes 2,3). In accordance with a DNA-based screening method, candidate compounds are incubated with a binding mixture including purified or partially purified NF-$AT_p$, Fos, and Jun and complex formation is detected in accordance with the foregoing. Candidate compounds which inhibit the formation of a NF-$AT_p$/Fos/Jun complex can be detected by viewing migration pattern on the gel.

Assays for screening candidate immunosuppressants that inhibit the association of NF-$AT_p$ with Fos and/or Jun proteins can also be non-DNA based. For example, detection of complex formation or inhibition of Fos and/or Jun protein binding can be accomplished by analyzing the mass of the complex formed in the presence or absence of a candidate compound using a sucrose gradient, in accordance with established techniques. See, e.g. *Current Protocols In Molecular Biology*, F. M. Ausubel. Ed., §5.3 (Greene Publishing Associates and Wiley Interscience, N.Y., 1989). Inhibition of binding of Fos and Jun proteins to NF-$AT_p$ can also be demonstrated by immunoprecipitating the binding reaction mixture, including a candidate compound, with antibodies to NF-$AT_p$, Fos, or Jun and detecting the presence or absence of complex formation. Antibodies to NF-$AT_p$ can be prepared as described; antibodies to Fos and Jun proteins are available commercially, and can also be readily prepared by persons skilled in art, using conventional techniques. Yet another method of identifying potential immunosuppressants from candidate compounds that inhibit or interfere with NF-AT complex formation involves protein cross-linking procedures known in the art. See, e.g. Diamond et al., *Science,* 249:1266.

In another embodiment, phosphorylation of purified NF-$AT_p$ by its naturally-occurring kinase may form the basis for an assay, with a compound that inhibits such phosphorylation having potentially significant effects on the activity of a T cell.

Other features and advantages of the invention will be apparent from the following Examples.

In the Examples and specification, the following abbreviations are used and have the meanings hereinafter identified: BSA, bovine serum albumin; CIP, calf intestinal phosphatase; CsA, cyclosporin A; DTT, dithiothreitol; EGTA, [ethylenebis(oxyethylenenitrilo)]-tetraacetic acid; Hepes, 4-(2-hydroxyethyl)-1-piperazineethanesulfonic acid; IL-2, interleukin-2; kDa, kilodalton; NF-AT, nuclear factor of activated T cells; NF-$AT_p$, preexisting subunit of the nuclear factor of activated T cells; NP-40, Nonidet P-40, PMSF, phenylmethylsulfonyl fluoride; SDS, sodium dodecyl sulfate; SDS-PAGE, sodium dodecyl sulfate-polyacrylamide gel electrophoresis.

METHODS

Cells:

The antigen-specific, murine T cell clone Ar-5 (Rao, A., Faas, S. J., and Cantor, H. (1984) *J. Exp. Med.* 159, 479–494) was maintained in Dulbecco's modified Eagle's medium supplemented with 10% fetal calf serum, 10 mM Hepes, pH 7.4, 2 mM glutamine, 50 μM 2-mercaptoethanol, 50 units/ml penicillin, 50 μg/ml streptomycin, and 5–10 units/ml partially purified rat IL-2 (Collaborative Research). The murine fibroblast L cell line was grown in Dulbecco's modified Eagle's Teedium supplemented with 10% fetal calf serum, 10 mM Hepes, pH 7.4, 50 units/ml penicillin, and 50 μg/ml streptomycin.

Preparation of cell extracts:

To prepare hypotonic extracts, cells were harvested by centrifugation, washed with phosphate buffered saline and resuspended to $10^8$ cells/ml in buffer containing 7.5 mM Tris (pH 7.6), 2 mM PMSF, 1 mM MgCl2, 0.5 mM DTT, 0.25 mM leupeptin, 0.1 mM EDTA and 1 mg/ml aprotinin. The cells were lysed by quick-freezing in dry ice and rapid thawing in a room-temperature water bath, followed by centrifugation at 12,000 x g for 10 minutes. Where indicated, cells were treated before harvesting with 1 μM CsA (Sandoz Corp.) or 100 nM FK506 (Fujisawa Pharmaceutical) for 10 minutes at 37° C.

In an alternative lysis protocol, extracts enriched for NF-$AT_p$ were prepared by lysing unstimulated T cells (2.5×$10^7$/ml) in a buffer containing 20 mM Tris pH 7.5, 10 mM iodoacetamide, 2 mM PMSF, 0.1 mM EDTA, 25 μM leupeptin, 100 μg/ml aprotinin and 0.05% NP-40. The cell lysates were first centrifuged at 200 x g to remove nuclei, and then centrifuged further at 100,000 x g for 60'. The 100,000 x g supernatant was made up to 1.5 M in ammonium sulfate, and the precipitated proteins were collected by centrifugation at 10,000 x g. The protein pellets were resuspended in buffer containing 100 mM NaCl, 20 mM Hepes, pH 7.4, 10 mM iodoacetamide, 2 mM EDTA, 2 mM PMSF, 25 μM leupeptin, 100 μg/ml aprotinin and 10% glycerol, and extensively dialyzed against the same buffer without iodoacetamide and with 0.5 mM DTT.

For preparation of nuclear extracts from activated T cells, cells were incubated for two hours with cross-linked anti-CD3ε monoclonal antibody (145-2C11, Kubo, R. T., Born, W., Kappler, J. W., Marrack, P., and Pigeon, M. (1989) *J. Immunol.* 142, 2736–2742) in the presence or absence of 1 μM CsA. Activation conditions and preparation of nuclear extracts was exactly as previously described (McCaffrey, P. G., Jain, J., Jamieson, C., Sen, R., and Rao, A. (1992) *J. Biol. Chem.* 267, 1864–1871). Protein determinations were done by the method of Bradford (Bradford, M. (1976) *Anal. Biochem.* 72,248–254), using bovine serum albumin as a standard.

Treatment of cell extracts with phosphatase in vitro:

Ammonium sulfate-precipitated protein (250 μg in 50 μl of buffer described above) were mixed with 1 μl calf intestinal phosphatase (Boehringer-Mannheim, 24 units/μl). For treatment with calcineurin, 250 μg of ammonium sulfate-precipitated protein was made up to 50 μl in 1.5 mM $MnCl_2$, 0.5 mM EDTA and 15 mM 2-mercaptoethanol. Purified bovine brain calcineurin (King, M. M., and Heiny, L. P. (1987) *J. Biol. Chem.* 262, 10658–10662) was added to 1 μM; calmodulin (Sigma) was added to 3 μM. All reactions were incubated at 30° C. for 10–15 minutes. The reactions were stopped by the addition of SDS-PAGE sample buffer and boiling, and the proteins were fractionated by SDS-PAGE as described below.

Fractionation of cell proteins by SDS-PAGE, elution and renaturation:

Hypotonic or nuclear extracts were boiled in SDS-PAGE sample buffer (65 mM Tris, pH 6.8, 2% SDS, 2% 2-mercaptoethanol, 10% glycerol, 0.01 mg/ml bromphenol blue) and fractionated on 3 mm thick SDS-polyacrylamide gels by standard methods (Laemmli, U. K. (1970) *Nature* 227, 680–685). Molecular weight standards (BioRad Laboratories) were also run on the same gel. After electrophoresis, the standards were cut off and separately stained. For recovery of proteins from the gels, slices (1 cm×0.5 cm) from wet, unfixed gels were crushed and eluted overnight in 50 mM Tris, pH 7.9, 1 mM DTT, 0.2 mM EDTA, 0.1 mM PMSF, 0.1 mg/ml BSA, 2.5% glycerol and 0.1% SDS (Baeuerle, P., and Baltimore, D. (1988) *Cell* 53, 211–217). The eluted proteins (250 μl) were precipitated with 4 volumes of acetone at −20° C., washed with methanol at −20° C., air dried and resuspendend in 2.5 μl of a saturated solution of urea. The urea was diluted with 125 μl of 20 mM Tris, pH 7.6, 10 mM KCl, 2 mM DTT and 0.1 mM PMSF, and the proteins were left overnight at 4° C. to renature. To assess the recovery of proteins from individual gel slices, aliquots of renatured proteins were electrophoresed on SDS-polyacrylamide minigels to separate the proteins derived from cell extracts from the carrier protein (BSA) added during elution. The gels were then stained using a sensitive silver stain procedure (Pierce Gelcode color silver stain kit), and the equivalent recovery of proteins from different gel slices was confirmed.

Electrophoretic mobility shift assay:

EMSAs were performed using 18 μl of renatured proteins in a 30 μl mix containing 4 mM Hepes, pH 7.4, 84 mM NaCl, 20 mM KCl, 0.08 mM EDTA, 9% glycerol, 0.7 mg/ml BSA, 17 μg/ml poly(dI:dC) and 0.125 ng of $^{32}$P-labelled oligonucleotide. For competition assays, a 200-fold excess of unlabeled oligonucleotide was added to the reaction. The reactions were incubated for 15 minutes at room temperature followed by electrophoresis at 4° C. on 4% Tris/borate/EDTA/acrylamide gels. The NF-AT oligonucleotide used had the sequence GCCCAAAGAGGAAAATTTGTTTCATACAG (SEQ ID NO:1), corresponding to the distal NF-AT site from the murine IL-2 promoter (nucleotides −295 to −267 relative to the transcription start site, (Serfling, E., Barthelmas, R., Pfeuffer, I., Schenk, B., Zarius, S., Swoboda, R., Mercurio, F., and Karin, M. (1989) *EMBO J.* 8, 465–473)). Oligonucleotides bearing mutations in the NF-AT site were as follows: M1, GCCCAAAGAGGAAAATTTGTTTATATCAG (SEQ ID NO:2); M2, GCCCAAAGAGGAAAATGGACTTCATACAG (SEQ ID NO:3); M3, GCCCAAAGACCTTAATTTGTTTCATACAG (SEQ ID NO:4); where underlined nucleotides indicate changes made from the NF-AT sequence.

Analysis of renatured purified NF-$AT_p$:

Cl.7W2 cell extracts were prepared by NP-40 lysis and ammonium sulphate precipitation as described above. The precipitated protein (1.2 g from $10^{11}$ cells) was dialyzed against buffer A [150 mM NaCl, 20 mM HEPES (pH 7.4), 2 mM EDTA, 0.5 mM DTT, 10% glycerol], supplemented with protease inhibitors (100 mg/ml aprotinin, 2.5 mM leupeptin and 2 mM PMSF) and loaded onto a 30 ml heparin-agarose column (Sigma). The column was washed with 10 column volumes of the same buffer containing 200 mM NaCl, and bound protein was eluted with a linear gradient of 0.2–1.0 M NaCl in a total volume of 250 ml. NF-$AT_p$ activity was determined by EMSA. Active fractions were combined and dialyzed overnight against Buffer A. The dialyzed pool (90 ml, 95 mg protein) was loaded in 20 mg batches onto a 1 ml high capacity oligonucleotide affinity column in the presence of 200 μg/ml sheared herring sperm DNA. The column was washed with the same buffer, and NF-AT was eluted with a linear gradient of 0.15–1.0 M NaCl. The NF-AT activity eluted in fractions between 0.4 M and 0.6 M NaCl. The peak fractions from several separate fractionations were combined, dialyzed against buffer containing 150 mM NaCl, and reloaded onto the same affinity column. After two cycles over the affinity column, approximately 10 μg of highly purified NF-$AT_p$ was obtained. This material bound specifically to the NF-AT site was a phosphoprotein substrate for calcineurin, and associated with c-Fos and c-Jun to form the NF-AT-Fos-Jun ternary complex on the NF-AT site oligonucleotide. Renaturation from gel slices and EMSAs were performed as described above. The purified NF-$AT_p$ protein was acetone precipitated, subjected to electrophoresis on a 6% SDS polyacrylamide gel, and transferred to nitrocellulose. The NF-$AT_p$ band was localized by Ponceau Red staining, excised, and digested with trypsin in situ. The resultant peptides were separated by microbore HPLC. Isolated proteolytic fragments were then analyzed by laser desorption mass spectroscopy, and microsequenced using an automated amino acid analyzer (Edman degradation).

Cloning of the gene encoding murine NF-$AT_p$:

Degenerate oligonucleotides based on the sequences of peptides 23.2 and 25 were used in a polymerase chain reaction to amplify an approximately 800-bp fragment from Cl.7W2 cDNA. The fragment was used to screen an amplified cDNA library (representing $10^6$ primary plaques) in the vector λZAPII (Stratagene) generated by oligo(dT) and random priming of cytoplasmic poly$(A)^+$ mRNA from Ar-5 T cells. After plaque purification of the recombinant λ bacteriophage clones and excision of pBluescript phagemids carrying the cDNA inserts, the coding sequences of several cDNA clones were determined by sequencing both strands using the dideoxy chain termination method well known in the art.

A cDNA fragment common to all the alternatively spliced cDNAs was excised by digestion with Xho I and Sma I, subcloned into the vector pQE-31 (Qiagen), and expressed as a hexahistidine-tagged protein in bacteria. The expressed protein contained an additional 18 vector-encoded amino acids, MRGSHHHHHHTAPHASSV (SEQ ID NO:6) at the $NH_2$-terminus, and 9 amino acids, VDLEPSLIS (SEQ ID NO:7) at the COOH-terminus, of the sequence indicated between the arrowheads in FIG. 10. The recombinant protein was purified by chromatography on a nickel-chelate column in 8 M urea, eluting with 250 mM imidazole. After dialysis against buffer A, the protein was assayed for DNA binding and Fos and Jun association.

In vitro transcription reactions:

Nuclear extracts were made from Namalwa cells (ATCC Accession No. CRL 1432) as described above. Fos and Jun proteins and truncated NF-$AT_p$ (NF-$AT_p$XS) were used at 500 μM and plasmid templates linearized by EcoRI were used at 80 μg/ml. Transcripts purified from the reactions were analyzed by polyacrylamide gel electrophoresis and quantitated using a phosphorimager.

Characterization of murine NF-$AT_p$:

To characterize the preexisting, DNA-binding component of NF-AT, we have used the murine IL-2 dependent T cell clone Ar-5. Activation of Ar-5 cells with monoclonal antibodies to the T cell antigen receptor or its associated CD3 complex causes the rapid appearance in the nucleus of several inducible transcription factor including NF-AT, which is followed by expression of the IL-2 gene and cell proliferation (Jamieson, C., McCaffrey, P. G., Rao, A., and Sen, R. (1991) *J. Immunol.* 147,416–420). Induction of NF-AT subsequent IL-2 gene expression are completely blocked by CsA and FK506 in these cells. We have previously established that unactivated Ar-5 cells contain a protein or proteins, extracted under hypotonic lysis conditions, that can bind in the EMSA to an oligonucleotide comprising the distal NF-AT sequence from the murine IL-2 promoter. Here we will refer to this NF-AT binding activity as NF-$AT_p$, to designate it as the subunit of NF-AT that is preexisting before T cell activation.

NF-$AT_p$ can be detected as an approximately 120 kDa protein after renaturation from SDS-polyacrylamide gels:

To determine an approximate molecular weight for NF-$AT_p$, we took advantage of the fact that some DNA-binding proteins retain their ability to bind DNA after elution from SDS-PAGE gels and renaturation (Baeuerele and Baltimore (1988), *Cell,* 53:211–217 Briggs, M. R., Kadonaga, J. T., Bell, S. P., and Tjian, R. (1986) *Science* 234, 47–52). Hypotonic extracts from unstimulated Ar-5 T cells were fractionated by SDS-PAGE, followed by elution and renaturation of proteins from individual gel slices as described. As a negative control, we also tested extracts from a fibroblast cell line (L cells) that contained no detectable binding activity specific for the NF-AT oligonucleotide before fractionation. The renatured proteins were assayed for DNA-binding by EMSA using an oligonucleotide spanning the distal NF-AT site of the murine IL-2 promoter. In T cell extracts, binding activity was detected in several slices containing proteins of apparent molecular weight 120 kDa and lower (See FIG. 1A, slices 6–16). In L cell extracts, binding was detected using renatured proteins from the molecular weight range 66 kDa and lower (slices 11–18 of FIG. 1A).

Since NF-AT expression has been reported to be restricted largely to T and B cells (Verweij, C. L., Guidos, C., and Crabtree, G. R. (1990) *Journal of Biological Chemistry* 265, 15788–15795) and we did not detect NF-AT binding in unfractionated L cell extracts, we considered the proteins of molecular weight lower than 66 KDa to be unlikely candidates for NF-$AT_p$.

Figure 2A:
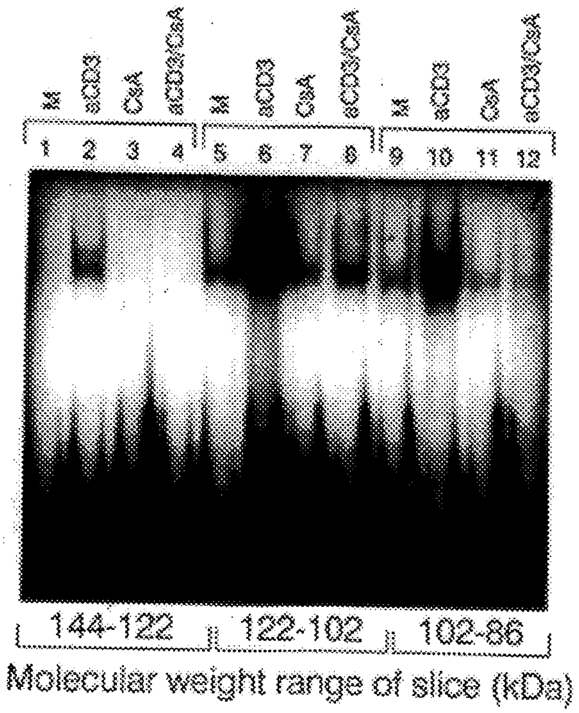
FIGS. 2A and 2B are photographs of SDS-PAGE gels in which NF-AT-binding proteins were detected in T cell nuclear extracts after renaturation from SDS-polyacrylamide gels.

Since nuclear extracts from activated T cells were expected to contain NF-$AT_p$ as part of the multisubunit nuclear NF-AT complex, we asked whether such extracts contained NF-AT-binding proteins that were detectable after renaturation from SDS-polyacryamide gels. Nuclear extracts containing NF-AT were prepared from Ar-5 T cells stimulated with an activating monoclonal antibody that reacts with the CD3ε subunit of the T cell antigen receptor/CD3 complex; these extracts were compared with nuclear extracts from unstimulated cells or cells stimulated in the presence of 1 μM CsA that do not contain appreciable levels of NF-AT. After fractionation of nuclear extracts by SDS-PAGE, DNA-binding proteins were detected primarily in gel slices containing proteins of apparent molecular weight 102–122 and 86–102 kDa (FIG. 2A, lanes 5–12), and weakly in the gel slice containing proteins of 122–144 kDa (FIG. 2A, lanes 1–4). An additional faint protein-DNA complex with a slower mobility was detected in the proteins from the 122–144 kDa range (lane 2); this complex is discussed below. Nuclear extracts from stimulated T cells, which contain high levels of NF-AT, yielded the highest levels of DNA-binding proteins after fractionation on SDS-PAGE gels (compare lane 6 with lanes 5 and 8 of FIG. 2A). The yield of total protein from gel slices of each sample was equivalent as assessed by SDS-PAGE and silver staining of the renatured proteins (data not shown; see Methods). In contrast to the results shown for hypotonic lysates, no additional DNA-binding proteins were detected in the lower molecular weight region of fractionated nuclear extracts (data not shown), suggesting that only the proteins in the 86–144 kDa range of both hypotonic and nuclear extracts contained NF-$AT_p$.

Figure 2B:
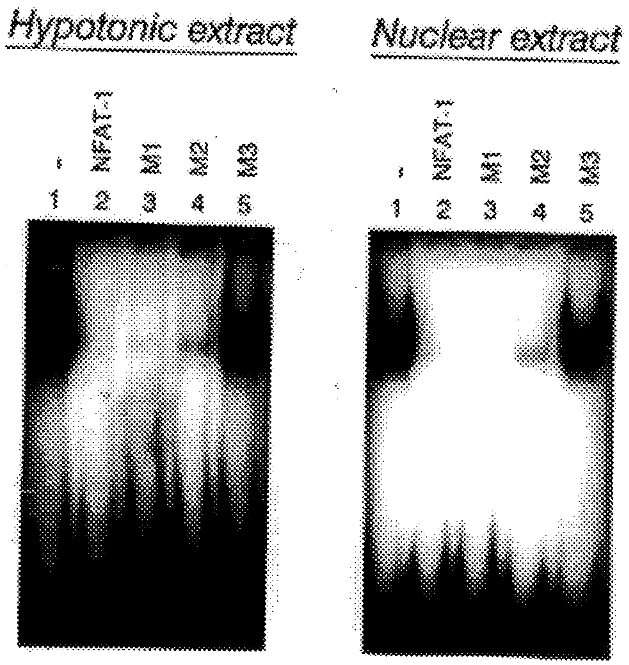

The renatured DNA-binding proteins (90–140 kDa) from nuclear and hypotonic extracts were tested for binding specificity for the NF-AT oligonucleotide by competition with oligonucleotides containing intact or mutated NF-AT sequences (FIG. 2B). By using these oligonucleotides in competition assays, we had previously defined a region in the distal NF-AT sequence critical for binding of both NF-AT and NF-$AT_p$ (Jain et al., *Nature,* 356:801–804). The M3 mutation disrupts this region, and thus this oligonucleotide fails to bind NF-AT (Jain, J., Miner, Z., and Rao, A., 1993, *J. Immunol.* 151:837–848) or to compete for NF-AT binding to the unmutated oligonucleotide. The M1 mutation has no effect on the ability of the oligonucleotide to bind NF-AT, while M2 slightly impairs NF-AT binding.

Similarly, the renatured proteins from either unactivated (hypotonic extract, FIG. 2B) or activated (nuclear extract, FIG. 2B) Ar-5 cells that bound to the NF-AT oligonucleotide were completely competed by the NF-AT oligonucleotide itself and by the M1 oligonucleotide, partially competed by the M2 oligonucleotide, and not competed at all by the M3 oligonucleotide. Thus, the 90–140 kDa proteins renatured from hypotonic extracts of unactivated T cells or nuclear extracts of activated T cells displayed the same binding specificity as previously demonstrated for $NF-AT_p$ and NF-AT. In contrast, the lower molecular weight DNA-binding proteins from either T cells or L cells were competed poorly by either the intact or mutated NF-AT oligonucleotides, indicating that they did not interact specifically with the critical binding region of the NF-AT sequence defined by M3, and thus did not contain $NF-AT_p$.

Figure 3:
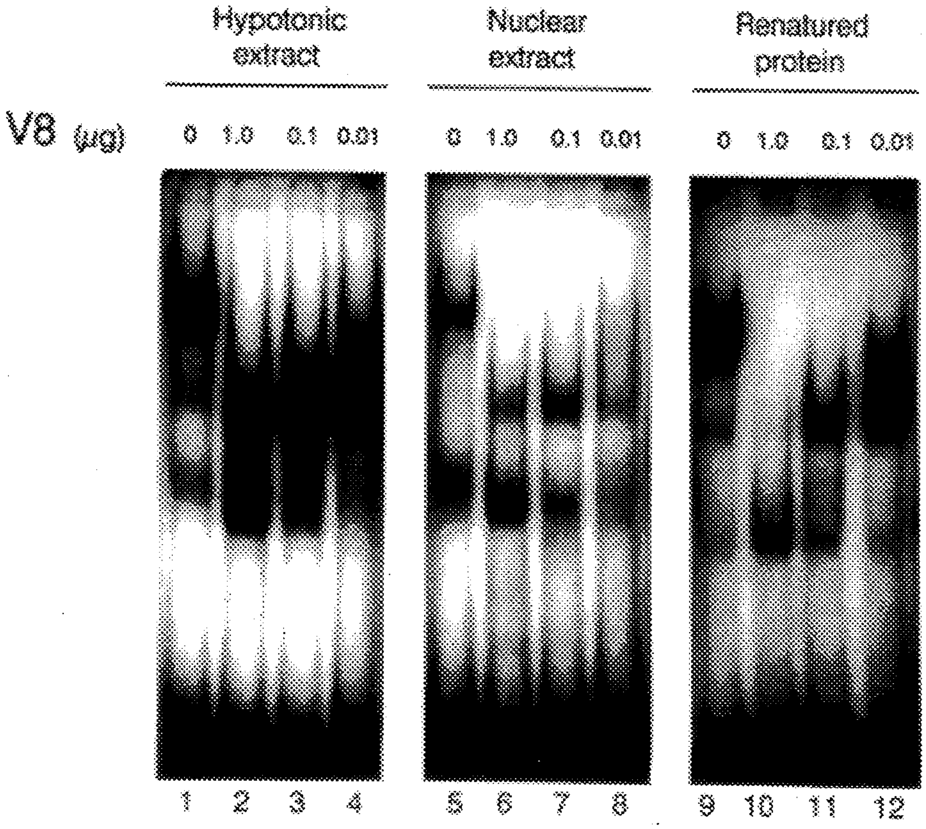
FIG. 3 is a photograph of an EMSA gel showing that NF-AT-binding proteins derived from V8 protease treatment of hypotonic or nuclear extracts are similar to those derived from NF-$AT_p$ renatured from SDS-acrylamide gels. Hypotonic extract, nuclear extract, or NF-AT-binding protein renatured from hypotonic extract, were mixed with increasing amounts of V8 protease as indicated, followed by addition of binding buffer, dI:dC, and labelled NF-AT oligonucleotide for the EMSA. The mixtures were incubated for 15 minutes at room temperature, and then subjected to gel electrophoresis at 4° C. Because the gel was run at 4° C., a more slowly migrating nuclear form of NF-AT (composed of NF-$AT_p$ plus Fos and Jun proteins) is faint in this gel (lane 5), but the same results are obtained when electrophoresis is done room temperature where the larger complex is more apparent.

Protease mapping experiments also provided evidence that the renatured proteins contained $NF-AT_p$. Treatment of hypotonic or nuclear extracts from Ar-5 cells with increasing amounts of V8 protease resulted in generation of two new major DNA-protein complexes in the gel shift assay (FIG. 3, lanes 1–8). These new complexes presumably represent the binding of proteolytic fragments of $NF-AT_p$ that retain their ability to interact with DNA. In agreement with this idea, V8 protease treatment of gel fractionated, renatured proteins from hypotonic extracts (FIG. 3, lanes 9–12) or nuclear extracts (data not shown) caused generation of similar DNA-binding fragments. In addition, treatment of extracts or renatured proteins with chymotrypsin generated a set of DNA binding fragments distinct from those generated by V8 but similar to each other. Protease treatment of nuclear extracts from unactivated cells that do not contain much $NF-AT_p$ (see FIG. 2A) does not result in generation of any new DNA-protein complexes. In addition, neither V8 nor chymotrypsin alone had any detectable DNA-binding activity in the gel shift assay. Thus, the new DNA-protein complexes detected after protease treatment of crude extracts are most likely derived from $NF-AT_p$, and the similarity between the pattern seen with nuclear, hypotonic or renatured proteins is consistent with the idea that the NF-AT-binding proteins in the renatured samples are related to the $NF-AT_p$ polypeptides detected in the original nuclear and hypotonic extracts.

These results indicate that $NF-AT_p$, the DNA-binding subunit of NF-AT that is present in unstimulated cells and appears in nuclear extracts upon T cell activation, migrates in SDS gels as a broad band of apparent molecular weight 90–140 kDa. By measuring the DNA-binding activity recovered in the 90–140 kDa region of the SDS-polyacrylamide gel, and comparing it to the activity in the extracts originally loaded, we determined that the overall yield of $NF-AT_p$ activity in the renaturation procedure was approximately 3%, a value consistent with the yield reported previously for elution and renaturation of the transcription factor Sp1. We could also renature $NF-AT_p$ after non-equilibrium pH gradient gel electrophoresis (NEPHGE, O'Farrell, P. Z., Goodman, H. M., and O'Farrell, P. H. (1977) *Cell* 12:1133). In this system, $NF-AT_p$ also migrated as a single broad band, suggesting that it is composed of a family of related proteins, or post-translationally modified variants of a single protein, or both.

Figure 4A:
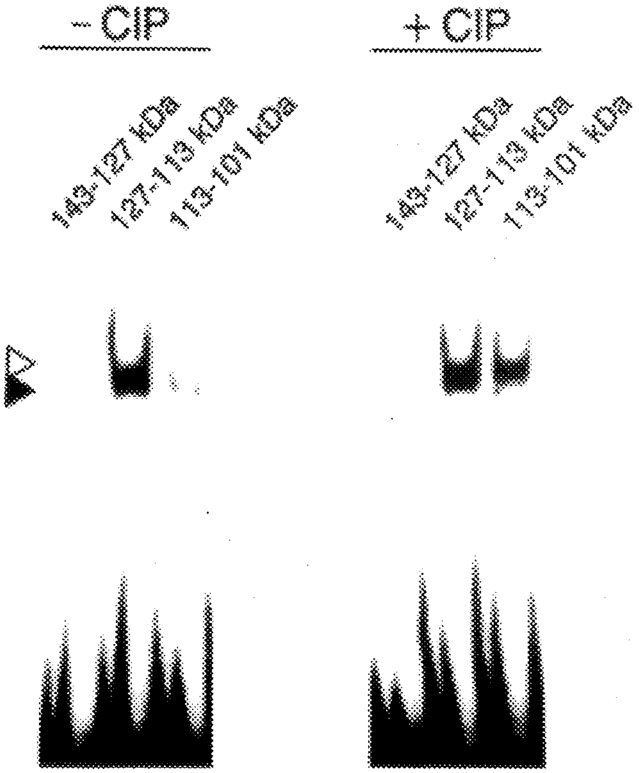
FIGS. 4A and 4B are photographs of an EMSA gel showing the effect of treatment of NF-$AT_p$ with exogenous phosphatases. A shift in NF-$AT_p$ mobility was observed on polyacrylamide gels. NP-40 extracts of Ar-5 cells were ammonium sulfate precipitated to enrich NF-$AT_p$ proteins, and the resulting proteins were treated with calf intestinal phosphatase (CIP) (FIG. 4A) or calcineurin (CaN) (FIG. 4B) as detailed below. The proteins were then fractionated on SDS-PAGE gels, eluted from individual gel slices spanning the molecular weight ranges indicated, renatured and assayed for binding to the NF-AT oligonucleotide. The solid arrow denotes NF-$AT_p$, while the open arrow denotes a minor complex appearing in the slice containing proteins of molecular weight 127–143 kDa.

$NF-AT_p$ is a phosphoprotein:

Since phosphorylation is a common source of protein size heterogeneity on SDS gels, and has important functional consequences for DNA-binding proteins, we examined the effect of exogenously added phosphatase on $NF-AT_p$ in cell extracts. In initial experiments, hypotonic extracts prepared by freeze-thawing and incubated for 10 min at 30° C. in the presence or absence of calf intestinal phosphatase yielded $NF-AT_p$ migrating in the 90–120 kDa molecular weight range. When extracts were prepared by an alternative procedure involving NP-40 lysis and enrichment of $NF-AT_p$ by ammonium sulfate precipitation, $NF-AT_p$ was recovered predominantly in the 113 to 127 kDa molecular weight fraction, and also to a small extent in the 127–143 kDa and 101–113 kDa fractions (FIG. 4A, left panel, –CIP). Treatment of the extracts with calf intestinal phosphatase (FIG. 4A, right panel, +CIP) resulted in the disappearance of the $NF-AT_p$ complex (indicated by solid arrowhead) from the 127–143 kDa molecular weight fraction, and a concomitant increase in the intensity of the complex formed with proteins in the 101–113 kDa slice (FIG. 4A, right panel). An additional faint protein-DNA complex (FIG. 4A, left panel, open arrowhead) was detected using proteins in the 127–143 kDa molecular weight fraction. This complex binds the NF-AT oligonucleotide specifically, as judged by competition with intact or mutated oligonucleotides, but it does not shift in mobility on treatment with phosphatases (FIG. 4A and 4B) or CsA (see below). Although its relation to $NF-AT_p$ is unknown, it serves as a useful control for evaluating changes in the apparent molecular weight of $NF-AT_p$. These results demonstrate that $NF-AT_p$ is a phosphoprotein whose mobility in SDS-polyacrylamide gels can be altered by changes in its phosphorylation state.

Since $NF-AT_p$ has been proposed to be a target for the calcium and calmodulin-dependent phosphatase calcineurin (protein phosphatase 2B), we tested the effect of this phosphatase on the mobility of $NF-AT_p$ in SDS gels. Treatment of the ammonium sulfate precipitated proteins with purified bovine brain calcineurin (FIG. 4B) caused a decrease in the amount of the highest molecular weight form of $NF-AT_p$ and an increase in the lower molecular weight form, although the change was not as dramatic as that seen with calf intestinal phosphatase. These results suggest that $NF-AT_p$ can be a direct substrate for the phosphatase calcineurin in vitro.

Figure 4B:
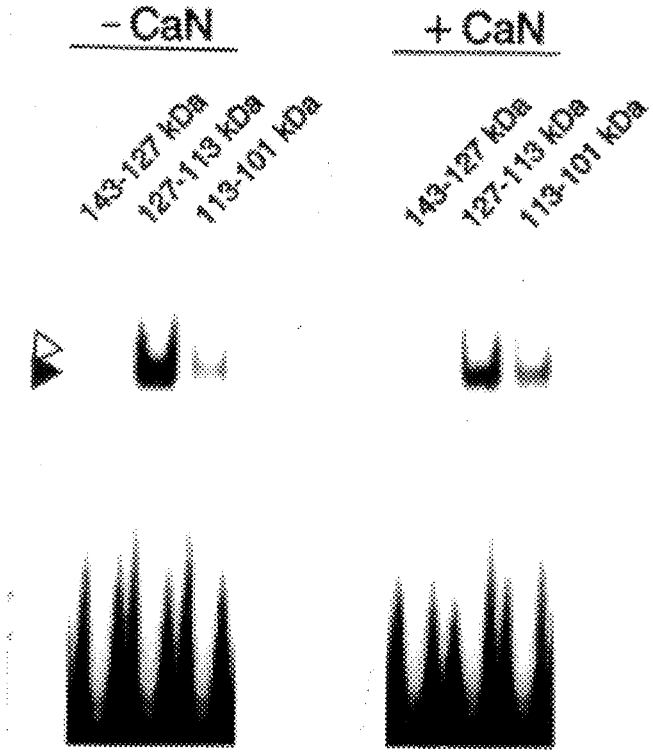
Figure 5A:
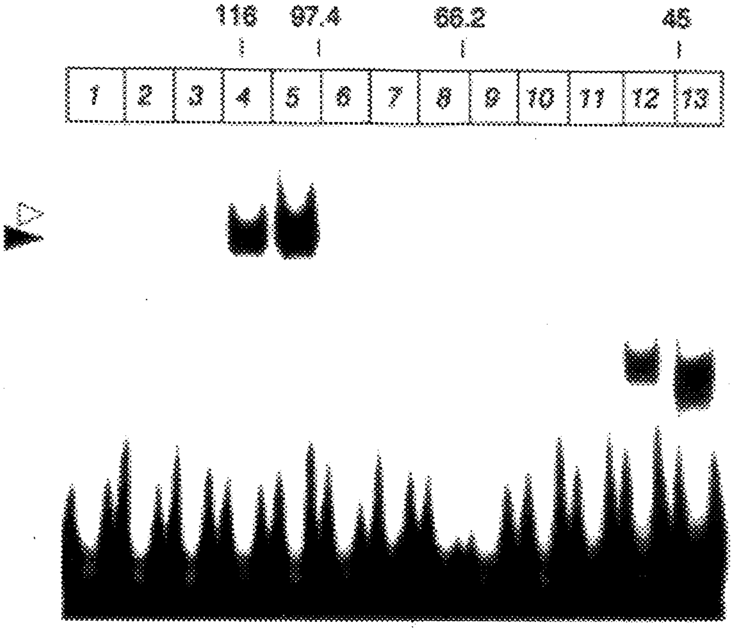
FIGS. 5A through 5C are photographs of EMSA gels showing that NF-$AT_p$ is a target for CsA. Hypotonic extracts (250 μg total protein) from untreated Ar-5 cells (FIG. 5A) or cells treated for 10 minutes with 1 μM CsA (FIG. 5B) were fractionated on SDS-acrylamide gels. Proteins were eluted and renatured from individual gel slices, and assayed for binding to the NF-AT oligonucleotide.
Figure 5B:
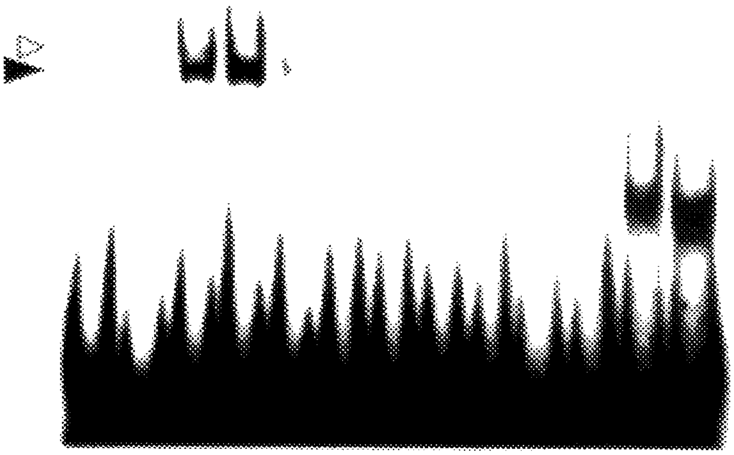
Figure 5C:
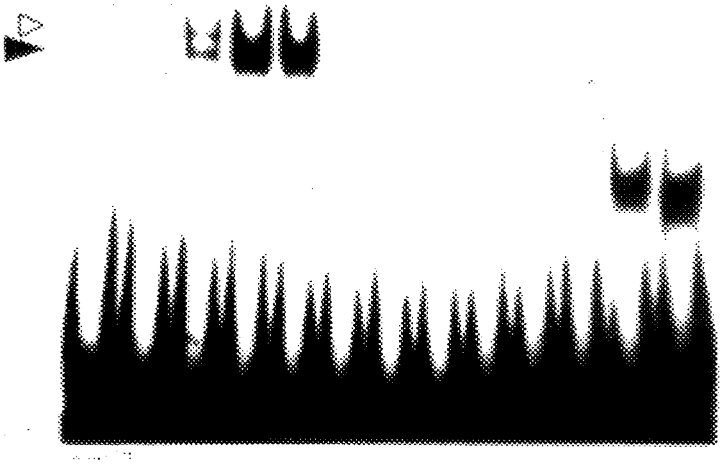

$NF-AT_p$ is a target for immunosuppressive drugs and calcineurin:

The ability of the immunosuppressive agents CsA and FK-506 to inhibit induction of NF-AT in activated T cells appears to result from their ability to inhibit the modification and perhaps the nuclear translocation of $NF-AT_p$. Recent studies have shown that CsA and FK506, in complex with their respective binding proteins (immunophilins), can inhibit the activity of calcineurin in vitro, and also that calcineurin is inhibited in cell lysates from cells treated with CsA or FK506 prior to lysis. To test whether the phosphorylation state of $NF-AT_p$ could be affected by treatment of cells with CsA, we treated cells for 10 minutes with or without CsA prior to lysis by freeze-thawing, and fractionated the extracts on SDS-polyacrylamide gels. For these experiments, we chose to lyse by freeze-thawing because our previous experiments showed that $NF-AT_p$ in such lysates would be predominantly in the lower molecular weight form (see FIG. 1 for example), and previous reports demonstrated that lysates made under similar conditions from human Jurkat T cells contained active calcineurin. As expected, extracts from untreated cells contained $NF-AT_p$ activity predominantly in gel slices corresponding to a molecular weight range of 99 to 111 and 111 to 125 kDa (FIG. 5A, lanes 4 and 5). In contrast, extracts from CsA-treated cells contained more activity in the 125–140 kDa range, and very little in the 99–111 kDa range (FIG. 5B, lanes 3 and 5). Similar results were seen after treatment of cells with FK506. This change in apparent molecular weight was specific for NF-$AT_p$, since proteins eluting in the lower molecular weight areas of the gel maintained their relative mobilities (see lanes 6–13). In addition, the change was specific for the predominant NF-$AT_p$ complex (solid arrowhead), and did not affect the faint upper complex (lane 3, open arrowhead), and thus was consistent with the sensitivity of the complexes to CIP and calcineurin treatment (FIG. 4A and 4B). The apparent change in molecular weight of NF-$AT_p$ upon CsA treatment was not due to the presence of inhibitors in the renatured proteins that masked binding activity, since mixed lysates contained activity in each slice in the range 99–145 kDa (FIG. 5C). The proteins detected in each slice bound specifically as shown by competition, and were shown to be related by protease mapping.

Figure 6:
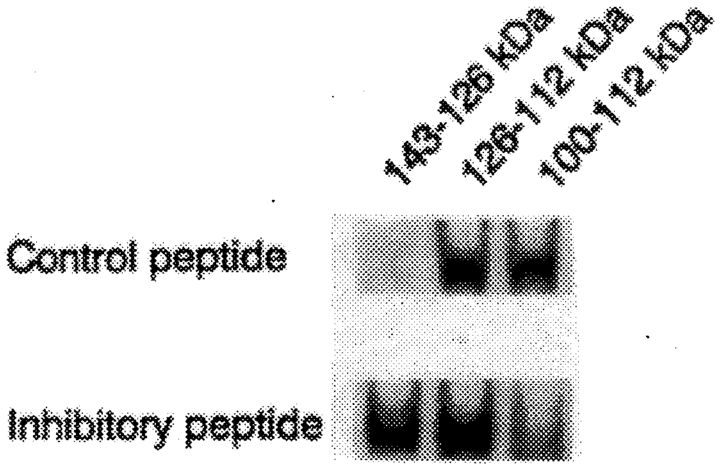
FIG. 6 is a photograph of a portion of an EMSA gel showing the results of an EMSA. The effect of a calcineurin inhibitor peptide on the mobility of NF-$AT_p$ is shown. Ar-5 cells were lysed by freeze-thawing in hypotonic buffer containing 100 μM of either a specific calcineurin inhibitory peptide ($IC_{50}$, 10 μM), or a control peptide containing a single amino acid substitution that does not inhibit calcineurin ($IC_{50}$>200 μM). The extracts (200 μg protein) were fractionated on SDS-acrylamide gels, and proteins were renatured from gel slices spanning the molecular weight ranges indicated (corresponding to lanes 3, 4 and 5 in FIGS. 5A–5C), and assayed for NF-AT binding. Only the portion of the gel shift gel containing the NF-$AT_p$-DNA complexes is shown.

To test directly whether activation of calcineurin during cell lysis was causing the appearance of the lower molecular weight form of NF-$AT_p$, we lysed cells in the presence of a specific peptide inhibitor of calcineurin (Hashimoto, Y., Perrino, B. A., and Soderling, T. R. (1990) *J. Biol. Chem.* 265, 1924–1927) or in the presence of a mutated peptide that lacked calcineurin inhibitory activity (Perrino and Soderling, unpublished results). Inhibition of calcineurin activity by inclusion of the specific peptide inhibitor in the cell lysis buffer resulted in the appearance of the higher molecular weight form of NF-$AT_p$, while lysis in the presence of the non-inhibitory (control) peptide resulted in detection of the lower molecular weight form (FIG. 6). Since our lysis buffer contained no EGTA, it was conceivable that the activation of calcineurin was resulting from calcium release during cell lysis. In agreement with this idea, inclusion of 2 mM EGTA in the cell lysis buffer resulted in recovery of the higher molecular weight form of NF-$AT_p$ (data not shown). Together, these results are consistent with the hypothesis that NF-$AT_p$ is a substrate for calcineurin in cell lysates, and that CsA and FK506 act to inhibit dephosphorylation of NF-$AT_p$ in cell lysates by inhibiting calcineurin.

Figure 8:
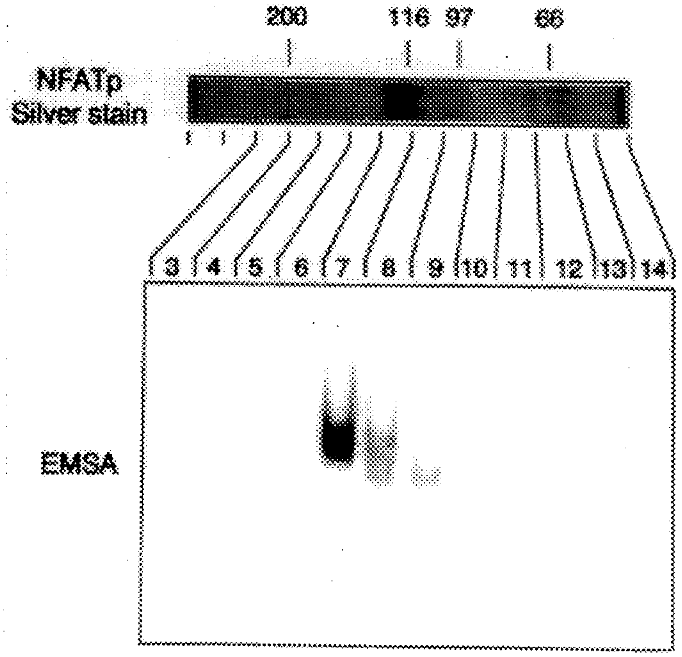
FIG. 8 is a photograph of an EMSA gel showing an analysis of NF-$AT_p$ by renaturation of NF-$AT_p$ activity following purification of the protein using SDS-polyacrylamide gel electrophoresis. In the top panel, purified NF-$AT_p$ (50 ng) was subjected to electrophoresis on an analytical 6% SDS-PAGE gel and subsequently silver-stained (Pierce Gel-code kit). In the bottom panel, a second lane of the same gel was loaded with 50 ng of the purified protein. After electrophoresis, the gel was sliced, proteins were eluted from gel slices and renatured, and the fractionated proteins were evaluated in an EMSA for their ability to bind to the NF-AT site of the murine IL-2 promoter.

Analysis of purified NF-$AT_p$:

NF-$AT_p$ was purified from the Cl.7W2 cell line, a derivative of the murine T cell clone Ar-5, by ammonium sulfate fractionation followed by successive chromatography on a heparin-agarose column and an NF-AT oligonucleotide affinity column. A silver-stained SDS gel of the purified protein showed a major broad band migrating with an apparent molecular weight of approximately 120 kDa (FIG. 8, top panel). This band contains a DNA-binding phosphoprotein that is dephosphorylated by calcineurin to yield four sharp bands migrating with apparent molecular weights of approximately 110–115 kDa. NF-$AT_p$ DNA-binding activity was demonstrable in protein eluted from the SDS gel and renatured, and more than 90% of the activity recovered from the gel comigrated with the approximately 120 kDa band (FIG. 8, lane 7). The faster-migrating complexes formed with proteins of slightly lower molecular weight (lanes 8–11) most likely derive from partial proteolysis. The purified protein binds to the NF-AT site with the appropriate specificity, and forms a DNA-protein complex with recombinant Fos and Jun.

Figure 9:
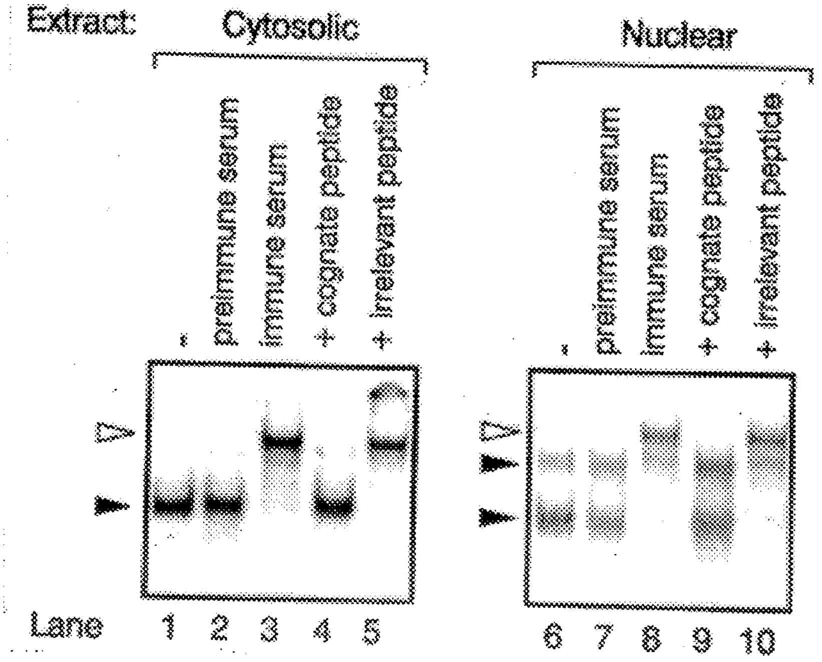
FIG. 9 is a photograph of an EMSA gel showing the results of an EMSA. Antisera to tryptic peptides of purified NF-$AT_p$ recognize NF-$AT_p$ in T cell extracts. Cytosolic extracts from unstimulated Ar-5 T cells (lanes 1–5) or nuclear extracts from Ar-5 T cells stimulated with anti-CD3 (lanes 6–10) were incubated without antiserum (lanes 1 and 6), with antiserum to peptide 72 (residues 206–227 of SEQ ID NO:5, see FIG. 10) (immune, lanes 3 and 8) or with serum from the same rabbit taken before immunization (preimmune, lanes 2 and 7), then analyzed by EMSA for binding to the NF-AT oligonucleotide. For peptide competition, 1 mg of peptide 72 (lanes 4 and 9) or peptide 25 (residues 685–703 of SEQ ID NO:5, see FIG. 10) (lanes 5 and 10) was mixed with the antiserum before it was added to cell extracts. Filled arrowheads identify the cytosolic NF-$AT_p$, nuclear NF-$AT_p$, and nuclear NF-$AT_p$/Fos/Jun complexes; open arrowheads indicate the "supershifted" complexes; the unmarked complex results from binding of serum proteins.

Antisera to tryptic peptides binds to NF-$AT_p$ in T cell extracts:

Antisera to tryptic peptides derived from the 120 kDa protein to confirm that the 120 kDa protein was the preexisting subunit of the T cell transcription factor NF-AT. When one such antiserum (raised against a 21-residue synthetic fragment containing residues 206–227 of peptide 72 shown in FIG. 10) was included in the binding reaction, it "supershifted" the NF-$AT_p$-DNA complex formed by the cytosolic fraction from unstimulated T cells (FIG. 9, lane 3), as well as both NF-AT complexes formed by nuclear extracts from stimulated T cells (lane 8). The effect of the serum was prevented by preincubation with its cognate peptide (lanes 4 and 9), but not by preincubation with a different peptide (lanes 5 and 10). Preimmune serum had no effect on binding (lanes 2 and 7). Similar effects were seen with antisera to peptides 23.1 and 25. These data demonstrate that the purified protein is NF-$AT_p$.

Identification of a murine NF-$AT_p$ cDNA clone.

In order to isolate a cDNA clone encoding NF-$AT_p$, degenerate oligonucleotides based on the sequences of two tryptic peptides of purified NF-$AT_p$ were used in a polymerase chain reaction (PCR) to amplify an approximately 800-bp fragment from Cl.7W2 cDNA, and the fragment was used to screen a cDNA library from murine T cells. The clone containing the longest cDNA insert, mNF-$AT_p$Q1B1/A, contains an insert of about 4.5 kb in length, with an open reading frame extending 2,672 bp from the 5' end of the insert and with about 1.8 kb of 3' untranslated region that does not extend to the poly(A) tail. The open reading frame encodes a polypeptide of 890 amino acids (SEQ ID NO:5) (FIG. 10) that contains eight of nine tryptic peptides identified by sequencing of purified NF-$AT_p$. The cDNA insert lacks a small amount of coding sequence at the 5' end, because the predicted molecular weight of the encoded protein (97 kD) is somewhat smaller than the apparent molecular weight of dephosphorylated NF-$AT_p$ (110–115 kD), and because one tryptic peptide from purified NF-$AT_p$ is unaccounted for in the encoded protein. A search of the GenBank DNA and protein databases with the Blast algorithm (Altschul et al., (1990) *J. Mol. Biol.* 215:403–410) indicated that the cDNA encodes a novel protein. A 464-amino-acid fragment containing the DNA-binding domain displayed a limited similarity to the rel homology domain of human and murine RelA (p65) (18.9% and 17.8% amino acid identity, respectively, over 428 amino acids). A preliminary analysis of additional cDNA clones indicates that T cells express at least three forms of NF-$AT_p$ related to each other by alternative splicing and differing at their COOH-termini.

Figure 11:
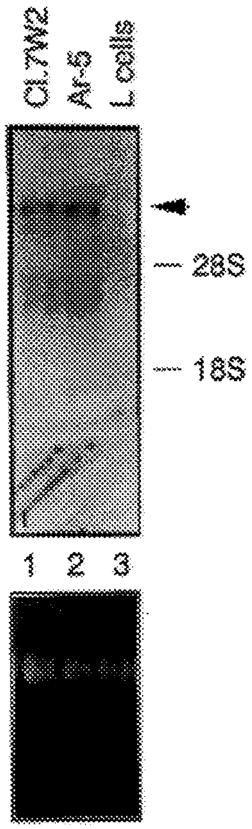
FIG. 11 is an autoradiograph of a Northern blot analysis of NF-$AT_p$ mRNA from T cell and fibroblast cell lines. Cytoplasmic RNA from the murine T cell clone At-5, the transformed T cell line Cl.7W2, and the murine fibroblast L cell line were separated by electrophoresis in formaldehyde gels, transferred to nylon membranes and hybridized with a labelled fragment of NF-$AT_p$ coding sequence corresponding to the approximately 800-bp PCR product. The positions of the major NF-$AT_p$ transcript (arrow) and of 28S and 18S ribosomal RNAs are indicated. The lower panel shows ethidium bromide staining of the RNA before transfer to nitrocellulose, indicating that the RNA was intact and that equivalent amounts of RNA were loaded in each lane.

Cell-specific expression of NF-$AT_p$ RNA:

Consistent with the previous demonstration that NF-$AT_p$ protein is present in T cells but not in L cells, the T cell lines Cl.7W2 and At-5, but not L cells, were found to express NF-$AT_p$ mRNA (FIG. 11). The PCR fragment of approximately 800 bp hybridized to a transcript of about 8–9 kb expressed in the Cl.7W2 T cell line used for purification of NF-$AT_p$ (lane 1) and in the untransformed T cell clone Ar-5 used to generate the cDNA library (lane 2), but did not hybridize to any transcript expressed in L cells (lane 3). Two other cDNA probes representing different parts of the coding region of NF-$AT_p$ gave similar results. Systematic analysis of the tissue distribution of NF-$AT_p$ can be accomplished by Western analysis, quantitative PCR, or Northern blot analysis.

Figure 12:
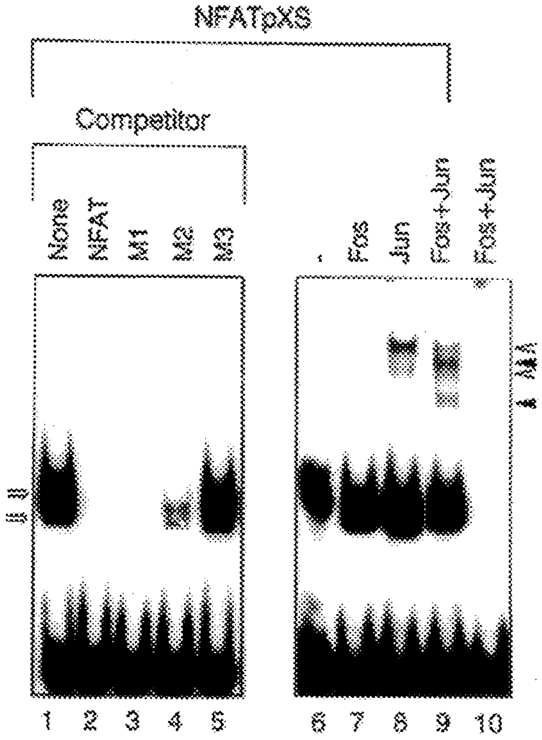
FIG. 12 is a photograph of an EMSA gel. Binding of a recombinant fragment of NF-$AT_p$ (NF-$AT_p$XS) to target DNA and association of the recombinant NF-$AT_p$ fragment with Fos and Jun proteins was evaluated. The binding of the recombinant fragment of murine NF-$AT_p$ to the distal NF-AT site of the murine IL-2 promoter was assessed by EMSA in the presence or absence of a 200-fold excess of unlabelled competitor oligonucleotides as shown in Lane 1–5. The arrows indicate two DNA-protein complexes formed with NF-$AT_p$XS. Full-length recombinant c-Fos and c-Jun proteins were included in the same binding reactions, as shown in Lanes 7–9. The open arrows indicate Jun—Jun-NF-$AT_p$XS complexes, while the closed arrows indicate Fos-Jun-NF-$AT_p$XS complexes. Fos and Jun proteins do not bind to the NF-AT oligonucleotide, as shown in Lane 10.

Binding specificity of recombinant murine NF-$AT_p$:

To test directly whether the cDNA encoded a protein with the characteristics of NF-$AT_p$, the ability of a recombinant fragment of the protein to bind to the NF-AT site of the murine IL-2 promoter and to associate with Fos and Jun was evaluated. Using the QIAexpress Kit (QIAGEN, Inc.), 464-amino-acid fragment of the protein (sequence between arrowheads in FIG. 10) (SEQ ID NO:20) was expressed as a hexahistidine-tagged protein in bacteria using the pQE31 vector. This recombinant protein bound to the NF-AT binding site oligonucleotide in a gel shift assay (FIG. 12, lane 1).

Its binding specificity was identical to that of authentic T cell NF-$AT_p$, as judged by competition with excess unlabeled NF-AT binding site oligonucleotide (lane 2) and the mutant NF-AT oligonucleotides M1–M3 (lanes 3–5). The M1 oligonucleotide (lane 3) is mutated in four bases remote from the NF-AT binding site, and competes as strongly for binding as the authentic NF-AT oligonucleotide; the M2 oligonucleotide (lane 4) is mutated in four bases located between the M1 and M3 regions, and competes with intermediate efficiency; and the M3 oligonucleotide (lane 5) is mutated in the GGAA tetranucleotide sequence essential for binding of NF-$AT_p$, and does not compete for binding. Methylation interference analysis also showed that binding of the recombinant protein to the NF-AT site required the GGAA core binding region, as previously demonstrated for NF-AT. Like NF-$AT_p$ purified from T cells, the recombinant protein associated with homodimers of c-Jun or with heterodimers of c-Fos and c-Jun, but not with c-Fos alone, to form a DNA-protein complex that migrated with slower mobility than the NF-$AT_p$-DNA complex in an EMSA (lanes 7–9). c-Fos and c-Jun do not bind to the NF-AT oligonucleotide in the absence of NF-$AT_p$ (lane 10). The complex containing c-Fos and c-Jun resembled the nuclear complex of NF-$AT_p$, Fos, and Jun in that its formation was competed by excess unlabeled AP-1 oligonucleotide. These data indicate that a fragment of NF-$AT_p$ of approximately 50 kDa is sufficient to account for the DNA binding properties of NF-$AT_p$ and for its ability to associate with Fos and Jun proteins.

Figure 13:
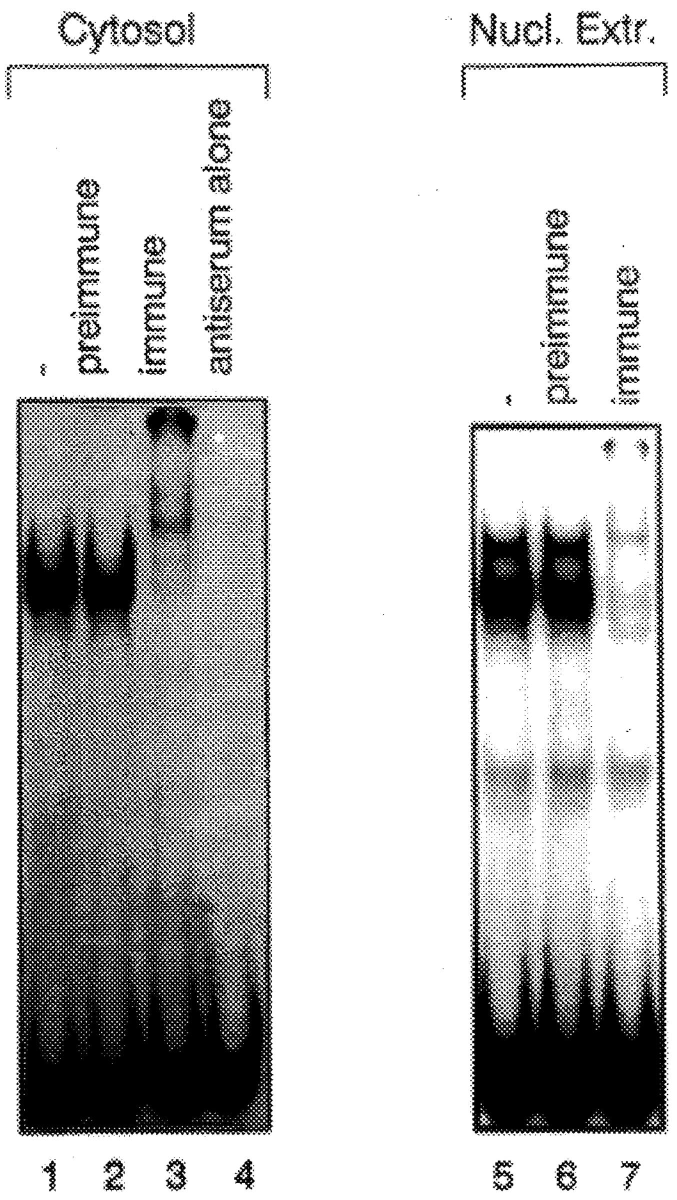
FIG. 13 is a photograph of an EMSA gel showing the results of an EMSA. Antisera to recombinant NF-$AT_p$ recognize NF-$AT_p$ in T cell extracts. Cytosolic extracts from unstimulated Ar-5 T cells or nuclear extracts from cells stimulated with anti-CD3 were incubated without antiserum (lanes 1 and 5), with an antiserum raised against the recombinant NF-$AT_p$ fragment (lanes 3 and 7), or with preimmune serum from the same rabbit (lanes 2 and 6), followed by gel shift analysis of binding to the NF-AT oligonucleotide.

Antisera to recombinant NF-$AT_p$ recognize NF-$AT_p$ in T cell extracts:

Definitive evidence that the cDNA clone encodes NF-$AT_p$ was provided by the ability of antisera to the recombinant protein to react specifically with NF-$AT_p$ from cytosolic or nuclear extracts of T cells. When serum from a rabbit immunized with the recombinant protein was included in the EMSA, a small proportion of the NF-$AT_p$-DNA complexes were "supershifted" (FIG. 13, lane 3) and most of the DNA-protein complexes appeared to be in large aggregates (lanes 3 and 7). The predominance of large aggregates probably reflects recognition by the serum of multiple antigenic determinants on NF-$AT_p$. Preimmune serum from the same rabbit did not alter the mobility of NF-$AT_p$-DNA and NF-AT-DNA complexes (lanes 2 and 6).

Transcriptional activation by NF-$AT_p$, c-Fos, and c-Jun on different templates.

Figure 14:
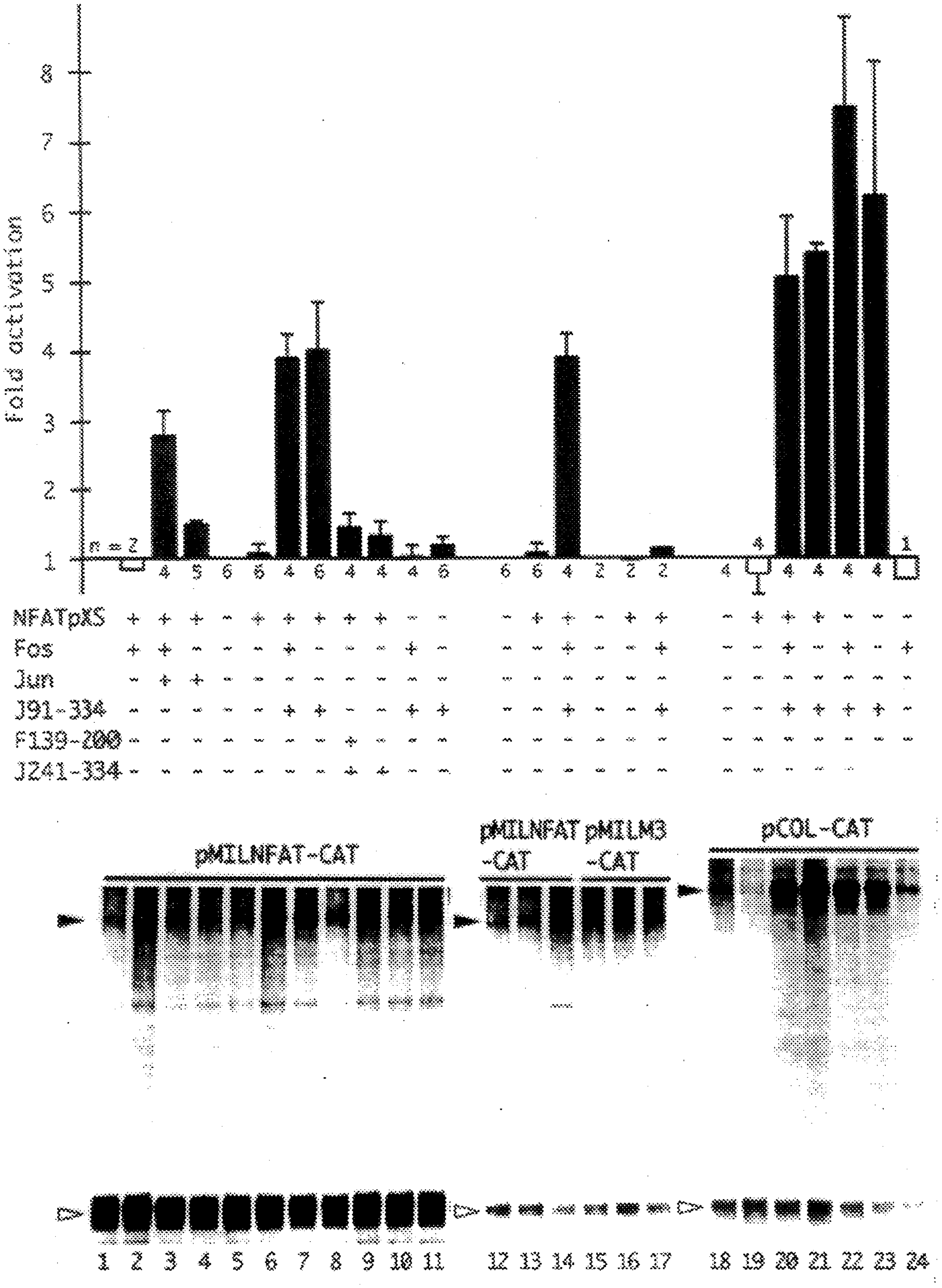
FIG. 14 is a photograph of RNA transcripts resolved on denaturing polyacrylamide gels and quantitated using a phosphorimager. Transcriptional activation by NF-$AT_p$, c-Fos and c-Jun on different templates was analyzed. The templates indicated above the lanes were incubated with the proteins listed and transcribed in vitro in nuclear extracts from Namalwa cells. The template pMILNFAT-CAT (lanes 1–14) contains three NF-AT sites upstream of the basal IL-2 promoter; the template pMILM3-CAT (lanes 15–17) contains four NF-AT sites in which critical contact residues have been altered; and the template pCOL-CAT contains residues −73 to +63 of the human collagenase promoter including an AP-1 site. The filled arrowheads point to the specific transcripts and the open arrowheads to internal controls. The level of transcription in the presence of different combinations of proteins was expressed relative to a reaction in the absence of recombinant proteins (fold activation). The average of several independent experiments (number shown at the base of each bar) and the standard deviation in cases in which more than three independent experiments were performed are shown (solid bars: activation; open bars: repression).

To examine the role of the cloned NF-$AT_p$ protein in transcription, the effect of the recombinant NF-$AT_p$ fragment on transcription in vitro from a template containing three NF-AT sites upstream of the murine IL-2 promoter was tested (FIG. 14). The same plasmid has been used to demonstrate transcriptional activation in vivo in response to stimulation with antigen (Jain et al., (1993), *J. Immunol.* 151:837). A combination of the recombinant NF-$AT_p$ fragment with c-Fos and c-Jun, or with c-Jun only, activated transcription from this construct (FIG. 14, lanes 2 and 3). In combination with NF-$AT_p$, a Jun deletion derivative (J91–334) lacking the amino-terminal repressor domain was a more potent activator than full-length Jun (lanes 6, 7, and 14), as previously observed for transcriptional activation by Jun at AP-1 sites (Kerppola et al., (1993), *Mol. Cell Biol.* 13:3782). In contrast, neither the truncated NF-$AT_p$ alone nor AP-1 proteins alone had a significant effect (lanes 5, 10, and 11). Truncated Fos and Jun proteins (F139–200 and J241–334) containing the dimerization and DNA-binding domains, but lacking transcriptional activation domains, are able to form a complex with NF-$AT_p$. However, the truncated proteins did not activate transcription in conjunction with truncated NF-$AT_p$ (lanes 8 and 9), indicating that the truncated NF-$AT_p$ is not transcriptionally active in the absence of Fos and Jun. No significant transcriptional activation was observed when a template containing a mutated NF-AT site incapable of binding NF-$AT_p$ was used (lanes 5–17). Moreover, the truncated NF-$AT_p$ had no effect on transcription activated by Fos and Jun on a template containing an AP-1 site (lanes 18–24), consistent with the observation that NF-$AT_p$ does not form a complex with Fos and Jun on the AP-1 site.

These data show that truncated NF-$AT_p$ forms a transcriptionally active complex with Fos and Jun at the IL-2 promoter NF-AT site, and are consistent with the interpretation that NF-$AT_p$ primarily determines the DNA-binding specificity of the NF-AT complex in vivo, whereas at least a portion of the transcriptional activity is provided by Fos and Jun. Since the current experiments were performed using a truncated NF-$AT_p$, they do not exclude the possibility that full-length NF-$AT_p$ possesses a transcriptional activation domain that can function in the absence of Fos and Jun. However, there is evidence suggesting that Fos and Jun family proteins are required along with NF-$AT_p$ to activate transcription at the IL-2 promoter NF-AT site in vivo, since mutations in the NF-AT site that prevent the association of Fos and Jun with NF-$AT_p$ abolish the function of this site in activated T cells.

The cDNA clone reported herein fulfills four essential criteria defining NF-$AT_p$: the mRNA is expressed in T cells but not in fibroblasts, a recombinant fragment of the protein binds specifically to the NF-AT site, the recombinant protein fragment forms a transcriptionally active complex with Fos and Jun on the NF-AT DNA sequence, and antibodies directed against the recombinant protein recognize NF-$AT_p$ in T cell extracts. The recombinant protein defines a functional 464-amino-acid fragment of NF-$AT_p$ that contains the domains required for DNA binding and for formation of a transcriptionally active complex with Fos and Jun. The cloning of this novel DNA-binding protein makes possible detailed studies of its structure, its interactions with other transcription factors and with specific sites in DNA, its role in the induction of IL-2 and other cytokine genes, and its regulation by calcineurin during T cell activation.

Murine NF-$AT_p$ isoforms:

FIG. 19 shows the partial cDNA sequence of murine NF-$AT_p$ from the cDNA insert of the deposited plasmid, mNF-$AT_p$-Q1B1/A (designated by "m") Additional cDNA clones of murine NF-$AT_p$ have been identified. Sequence analysis of the cDNA inserts revealed the existence of alternatively spliced isoforms of NF-$AT_p$. The alternatively spliced forms that have been isolated are identical in sequence to mNF-$AT_p$-Q1B1/A in the region up to and including nucleotide 2208 of mNF-$AT_p$-Q1B1/A (see FIG. 20).

Cloning of the human homolog of murine NF-$AT_p$:

Four fragments of the coding sequence of murine NF-$AT_p$ cDNA have been characterized for use as probes to isolate the human cDNA. Two are restriction fragments that can be prepared from plasmid mNF-$AT_p$-Q1B1/A: a fragment that extends from the EcoRI site in the multiple cloning site of the vector to the EcoRI site at nucleotide 570 of the insert ("EcoRI fragment"), and a fragment that extends from the PstI site at nucleotide 646 of the cDNA to the PstI site at nucleotide 1169 ("PstI fragment"). The third fragment which is approximately 800 bp ("~800 bp PCR product") is a cDNA fragment amplified from mouse T cell cDNA by the polymerase chain reaction (PCR), and which corresponds to the region between nucleotides 1314 and 2089 in plasmid mNF-$AT_p$-Q1B1/A. The fourth fragment corresponds to the region between nucleotides 1849 and 2089 in the plasmid, and is obtained from the ~800 bp PCR product by digestion with SphI ("SphI-3' fragment").

The cDNA probes described above are sufficient to identify human cDNAs representing the entire coding sequence of NF-$AT_p$, including cDNAs that have a region in common with these probes and encode isoforms of NF-$AT_p$ that are related by alternative splicing. The fragments specified for use as probes span the region common to all the splicing variants of NF-$AT_p$ cDNA that have been identified in the mouse T cell, with the exception of the extreme 5' end of the coding sequence, a region of the human cDNA that has been isolated already in human clone hNF-$AT_p$-21B2. Radiolabelled probes made from the EcoRI fragment, the PstI fragment, and the SphI-3' fragment form stable hybrids with a single human gene (under the same conditions used for screening cDNA libraries) as demonstrated directly by Southern hybridization to restriction enzyme-digested human genomic DNA. Specific binding of the EcoRI fragment and the SphI-3' fragment in a Southern hybridization is shown in FIG. 15 and 16, respectively.

Figure 15:
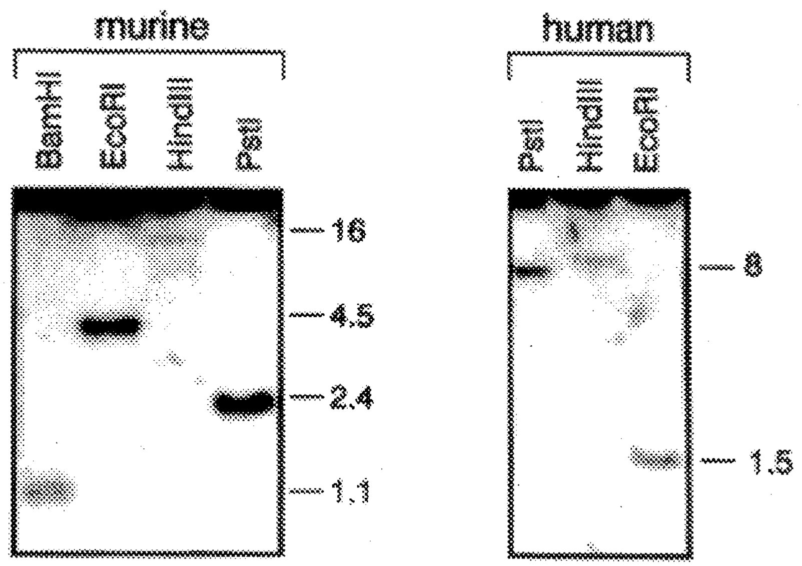
FIG. 15 is an autoradiograph of a Southern hybridization assay. A labelled probe made from the EcoRI fragment (described in text) of the murine NF-$AT_p$ cDNA, representing the 5' end of coding sequence contained in clone mNF-$AT_p$-Q1B1/A, hybridizes to specific restriction fragments of human genomic DNA. Hybridization of the same probe to restriction fragments of murine genomic DNA is shown for comparison.
Figure 16:
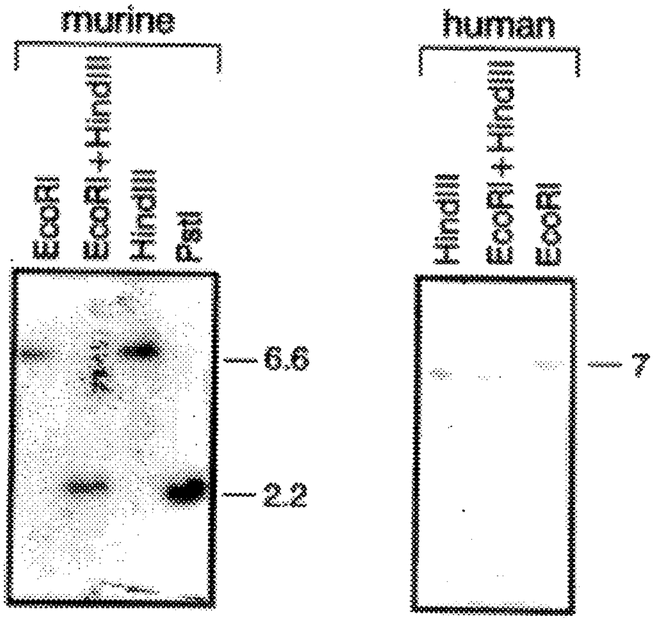
FIG. 16 is an autoradiograph of a Southern hybridization assay. A labelled probe made from the SphI-3' fragment (described in text) of the murine NF-$AT_p$ cDNA, representing the 3' end of coding sequence common to all alternatively spliced forms of murine NF-$AT_p$, hybridizes to specific restriction fragments of human genomic DNA. Hybridization of the same probe to restriction fragments of murine genomic DNA is also shown.

The experiment shown FIG. 15 and 16 indicates that these murine cDNA probes satisfy the two essential conditions for their use in screening human cDNA libraries: the probes form DNA hybrids with the human sequences that are sufficiently stable to survive washing under moderate stringency or high stringency conditions; and they do not label multiple DNA fragments in human genomic DNA, indicating that a high background of false positive signals (due to nonspecific hybridization or hybridization to repeated sequences) is unlikely to occur in screening the cDNA libraries.

The EcoRI fragment probe from mouse cDNA has been used to isolate a partial length cDNA encoding human NF-$AT_p$ (hNF-$AT_p$-21B2) from a human Jurkat T cell cDNA library, further demonstrating that the murine cDNA probes can efficiently identify human cDNA clones containing NF-$AT_p$ coding sequences. Since the EcoRI fragment identifies a single gene in Southern analysis of human genomic DNA, it was likely a priori that the hNF-$AT_p$-21B2 cDNA represented human NF-$AT_p$. Direct evidence that this clone encodes human NF-$AT_p$ is that the predicted sequence of the encoded protein is ~90% identical at the amino acid level to that of mouse NF-$AT_p$ (encoded by mNF-$AT_p$-Q1B1/A) in the region of overlap, which extends for 243 amino acids. Further, the coding sequence of hNF-$AT_p$-21B2 cDNA in the region 5' to its overlap with the known mouse NF-$AT_p$ sequence encodes a peptide very closely related (identical at 30/32 positions) to a tryptic peptide of purified NF-$AT_p$ protein from mouse T cells. Although this peptide was known from microsequencing of the purified mouse protein, it is not encoded in the partial length mouse cDNA mNF-$AT_p$-Q1B1/A, and was therefore expected to be encoded near the 5' end of the NF-$AT_p$ coding sequence.

In a parallel strategy to identify human NF-$AT_p$ cDNA clones, a fragment of the human cDNA that represents the 3' end of the partial-length cDNA already obtained can be used to screen the human T cell cDNA libraries. A suitable KpnI-EcoRI restriction fragment can be prepared from plasmid hNF-$AT_p$-21B2. This cDNA fragment extends from a KpnI site in the cDNA insert (corresponding to the KpnI site at nucleotide 369 of the mouse cDNA) to the EcoRI site in the multiple cloning site of the pBluescript vector. This KpnI-EcoRI fragment of the human cDNA overlaps the EcoRI fragment of mouse cDNA, and offers the slight advantage that replica filters of the cDNA library can be washed at even higher stringency than is possible with the mouse cDNA probes.

Using reagents derived from the mouse cDNA clone mNF-$AT_p$-Q1B1/A and the human cDNA clone hNF-$AT_p$-21B2, the isolation of a full-length human NF-$AT_p$ cDNA is well within the skill of those skilled in the art of molecular biology. For example, radiolabelled cDNA probes made from the cDNA inserts of murine clone, mNF-$AT_p$-Q1B1/A, and human clone, hNF-$AT_p$-21B2, can be used to identify and isolate cDNAs, present in cDNA libraries from human T cells that contain regions with sequence homology to these cDNAs. The following paragraphs describe murine cDNA probes that have been demonstrated to form sufficiently stable hybrids with human NF-$AT_p$ DNA for efficient screening of cDNA libraries; a human cDNA probe for screening cDNA libraries; the availability of cDNA libraries from human T cells; the specific methods that will be used to isolate cDNAs encoding human NF-$AT_p$; and the methods for characterization of these cDNAs.

Preparation and labelling of cDNA probes for isolation of full-length human NF-$AT_p$ clone:

Restriction fragments can be prepared from the plasmids mNF-$AT_p$-Q1B1/A and hNF-$AT_p$ -21B2 by digestion with the restriction enzyme(s) (EcoRI; PstI; or KpnI and EcoRI) specified above, and purified by agarose gel electrophoresis in low-melting-temperature agarose, followed by excision of the appropriate ethidium-bromide-stained band, and recovery of DNA from the agarose using methods well known in the art (Sambrook et al, supra). The purified DNA probe can then be radiolabelled by a random priming method using a kit supplied by Boehringer Mannheim, according to a protocol from Boehringer Mannheim.

The ~800 bp PCR product and its SphI-3' fragment can be prepared using routine methodology in the following sequence of steps: preparation of RNA; synthesis of cDNA; PCR amplification; and digestion with restriction enzyme. RNA can be isolated from mouse T cells, and enriched for mRNA by selection on oligo(dT)-cellulose (Sambrook et al., supra).

cDNA can be synthesized using random hexanucleotide primers by known methods, briefly described as follows. In a silanized tube, 1 μg poly(A)$^+$ RNA (obtained by selection on oligo(dT)-cellulose) and 100 pmol random hexanucleotides (Pharmacia) are mixed in a total volume of 10 μl RNase-free water. The tube is heated at 95° C. for 3 min., chilled on ice, and centrifuged to bring all the liquid to the bottom of the tube. Then 10 μl of a reaction mixture [2x MMLV buffer (GIBCO-BRL); 20 mM DTT; 2 mM of each of the 2'-deoxynucleoside 5'-triphosphates dATP, dCTP, dGTP, dTTP (Ultrapure dNTP Set, Pharmacia); and 20 U/μl MMLV reverse transcriptase (GIBCO-BRL)] is added, the reaction is incubated at 22° C. for 10 min, and further incubated at 42° C. for 60 min. PCR amplification primed by the oligonucleotides shown below is performed in a 100 μl reaction volume [containing 20 mM tris HCl, pH 8.3 at 20° C.; 25 mM KCl; 2 mM $MgCl_2$; 100 μg/ml BSA; 40 pmol of each oligonucleotide primer; 50 μM of each of the 2'-deoxynucleoside 5'-triphosphates dATP, dCTP, dGTP, dTTP; 2 U Taq polymerase (Perkin-Elmer Cetus); and 1 μl cDNA from the above cDNA synthesis reaction]. After preparation of the reaction mixture it is overlaid with mineral oil, and subjected to the following series of steps in a thermal cycler: 3 min at 72° C.; 5 min at 95° C.; 30 sec at 55° C.; then 35 sequential cycles [2 min at 72° C.; 30 sec at 95° C.; 30 sec at 55° C.]; then 5 min at 72° C. This typical PCR protocol is based on that recommended by Innis MA and Gelfand DH, (1990), Optimization of PCRs, In *PCR Protocols*, Innis MA, Gelfand DH, Sninsky JJ, and White, TJ, editors, Academic Press (San Diego). Digestion with SphI, purification of the SphI-3' fragment by agarose gel electrophoresis, and radiolabelling of the DNA fragment can be performed using procedures described above.

The following sequences of degenerate oligonucleotide primers can be used in preparation of the ~800 bp PCR product:

5'-CGTTCGGATCCAGTGTT(TC)ATGGAGAA(AG) ACTACA-3' (SEQ ID NO:9) 5'-CGACAGGATCCTG (TC)TGIATIACIGTIGG(GA)TA(CTGA)GC-3' (SEQ ID NO:10). The upper sequence is that of the sense strand primer, and the lower sequence that of the antisense strand primer. "A", "C", "G", and "T" are the standard single-letter abbreviations for the nucleotide bases; "I" represents inosine; letters enclosed in parentheses represent sequence degeneracy, and indicate which bases are present at that position in the oligonucleotide. Bold type represents the portion of the primer that is expected to anneal to NF-$AT_p$ coding sequence; the remainder of each oligonucleotide incorporates a restriction site and a "GC clamp". Although primers exactly matched to the known sequence of the murine cDNA would be expected to yield the same product, the PCR conditions described have been developed for these degenerate primers, and routinely give the desired product.

Since the present application discloses both murine and human NF-$AT_p$ sequence and makes available plasmids containing such sequence, obtaining the complete sequence of NF-$AT_p$ is a simple matter of applying routine hybridization techniques to one or more appropriate cDNA libraries (e.g., T cell cDNA libraries). To ensure that a full-length cDNA or overlapping cDNAs representing the entire coding sequence will be obtained, more than one cDNA library of 1–5 million independent clones can be screened. Several cDNA libraries from human T cells are available from commercial sources, e.g., Clontech.

In the event that it becomes necessary to prepare additional cDNA libraries from human T cells for the purpose of obtaining a full-length cDNA clone, cDNA libraries with greater than 1 million independent clones can be prepared either by commercial services for a fee (for example, Stratagene, Inc. offers this service), or by a researcher in the laboratory using standard techniques and commercially available reagents (supplied, for example, by Stratagene, Inc. or by Promega) that have been optimized for the steps of cDNA synthesis, ligation to λ bacteriophage arms, packaging into λ bacteriophage particles, and infection of host cells. To ensure that the entire coding region of the NF-$AT_p$mRNA is represented, the cDNA can be synthesized both with oligo(dT) priming and with random priming.

Methods for screening cDNA libraries:

The screening of replica filters of cDNA libraries with radiolabelled cDNA probes is routine in the art of molecular biology. Plating of the cDNA library; preparation of replica filters; hybridization with radiolabelled probe and washing; identification of positive plaques by alignment of an autoradiograph of the filter with the original plate; and plaque purification of individual clones that contain cDNA hybridizing with the probe have been described in detail by Sambrook et al. supra.

Methods for isolation and sequence analysis of cDNAs.

The isolation and sequencing of a phage or plasmid clone previously determined to contain the cDNA of interest, i.e., human NF-$AT_p$, can be performed using routine methodology. For example, to isolate NF-$AT_p$ cDNA clones from libraries in the λZAPII vector, a pBluescript plasmid vector carrying the cDNA insert can be excised according to the protocol that is supplied by the manufacturer, e.g., Stratagene, Inc., with the vector or with commercially-available cDNA libraries made in the vector, λZAPII. Individual colonies of bacteria containing the resulting plasmid can be grown on ampicillin-containing medium, and plasmid DNA can be prepared by standard techniques (Sambrook et al, supra). If libraries made in other λ phage vectors are used, bacteriophage λ vector DNA containing the cDNA insert can be isolated from individual λ clones (after plaque purification) using known methods (Sambrook et al, supra), and digested using the appropriate restriction enzymes to obtain the cDNA insert or cDNA insert fragments. These cDNAs can then be subcloned into a plasmid vector (e.g., pBluescriptII), and the plasmid DNA purified by standard techniques. The sequence of each cDNA insert can be determined (on both strands) using the dideoxy chain termination method well known in the art (Sanger et al, supra; Sambrook et al, supra).

Identification and characterization of a human NF-$AT_p$ cDNA clone.

The plasmid hNF-$AT_p$-21B2 which has been deposited with the ATCC contains a cDNA insert representing a portion of the coding sequence of human NF-$AT_p$. FIG. 17 (SEQ ID NO:11) depicts a partial sequence of the cDNA insert of clone hNF-$AT_p$-21B2. "" denotes approximately 1.9 kb of cDNA insert, expected to be principally 5' untranslated region, that has not yet been sequenced. "" indicates a gap introduced in the human sequence to maintain alignment with the known murine sequence in the region of overlap. FIG. 18 (SEQ ID NO:12) shows the amino acid sequence deduced from the cDNA insert of hNF-$AT_p$-21B2.

FIG. 19 shows an alignment of the murine (SEQ ID NO:8) and human (SEQ ID NO:21) NF-$AT_p$ cDNA sequences in the region of overlap. The region of overlap corresponds to 732 bp at the 5' end of the murine cDNA insert. In this figure, "" indicates identity and "." indicates a gap introduced in the human sequence to maintain alignment with the murine sequence. This provisional human sequence appears to contain an in-frame stop codon, TGA, between bp 650–660 as shown in FIG. 19. Considering the homology between the human and murine sequences and the tryptic peptide data, this in-frame stop codon probably represents a sequencing error. Careful sequence analysis of the deposited human cDNA clone, hNF-$AT_p$-21B2, is likely to resolve the discrepancy.

Deposit

Under the terms of the Budapest Treaty on the International Recognition of the Deposit of Microorganisms for the Purpose of Patent Procedure, deposit of the following materials has been made with the American Type Culture Collection (ATCC) of Rockville, Md., USA.

Applicants' assignees, President and Fellows of Harvard University and Dana-Farber Cancer Institute, Inc., represent that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

Plasmid hNF-$AT_p$21B2 containing the human NF-$AT_p$ sequence and the plasmid mNF-$AT_p$-Q1B1/A containing the murine NF-$AT_p$ sequence have been deposited on Oct. 28, 1993 with the American Type Culture Collection (Rockville, Md.) and have received ATCC designations 75598 and 75597, respectively.

Alternative cloning strategies:

Since the amino acid sequence of purified NF-$AT_p$ has been determined, obtaining a full length NF-$AT_p$ clone and any alternatively spliced isoforms can be accomplished using any one of a number of techniques known to those skilled in the art. Such cloning techniques are described in detail in Molecular Cloning: A Laboratory Manual, Sambrook et al. 1989, Second Edition, Cold Spring Harbor Laboratory, Cold Spring Harbor, N.Y. Three well known alternative cloning strategies are described below.

Based on the amino acid sequence of purified NF-$AT_p$, two PCR primers of approximately 15 nucleotides can be synthesized corresponding to either end of a length of a NF-$AT_p$ peptide of approximately 40 amino acid residues. cDNA can be prepared from 100 mg of total RNA obtained from a cell previously determined to express NF-$AT_p$, e.g., AR-5 cells. The primers are added to the cDNA with standard PCR components and the mixture is incubated under standard PCR conditions. Amplified fragments can be separated by electrophoresis and subcloned into a sequencing vector, for example, Bluescript (Stratagene, La Jolla, Calif.), by blunt end ligation. Alternatively, restriction enzyme sites can be incorporated into the PCR primers and the PCR product digested with the appropriate restriction enzyme and ligated to a vector which has been digested with a restriction enzyme to produce compatible sticky ends. The PCR-derived NF-$AT_p$ insert DNA can be sequenced using known methods e.g., the dideoxy-chain-termination method, utilizing e.g., SEQUENASE® DNA polymerase (United State Biochemical Corp.) (Sanger F. et al., (1977), *Proc. Natl. Acad. Sci. USA* 74:5463–5467). DNA fragments so isolated can be used as hybridization probes to screen for overlapping cDNA inserts in a cDNA library prepared from cells known to express NF-$AT_p$, e.g., Ar-5 cells. Positive clones can be isolated and the DNA sequenced and compared with that of the available amino acid sequence. Oligonucleotide primers corresponding to bordering vector regions as well as NF-$AT_p$ primers prepared from previously isolated cDNA clones can be employed to progressively determine the sequence of the entire gene.

Fragments of DNA containing sequences that correspond to the amino acid sequence of NF-$AT_p$ can be recloned into an expression vector, using a variety of methods known in the art. For example, a recombinant NF-$AT_p$ polypeptide can be expressed as a fusion protein with maltose binding protein produced in *E. coli*. Using the maltose binding protein fusion and purification system (New England Biolabs), the cloned NF-$AT_p$ sequence can be inserted downstream and in frame of the gene encoding maltose binding protein (malE), and the malE-NF-$AT_p$ fusion protein can then be overexpressed. In the absence of convenient restriction sites in the NF-$AT_p$, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column. Alternatively, an antibody specific for the NF-$AT_p$ portion of the fusion protein can be immobilized on a column and the fusion protein purified by virtue of the NF-$AT_p$ portion of the protein binding to immobilized NF-$AT_p$ specific antibody or NF-AT oligonucleotide.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from recombinant NF-$AT_p$. The cleavage products can be subjected to further chromatography to purify the NF-$AT_p$ from the maltose binding protein.

The recombinant NF-$AT_p$ can be tested for functional activity, such as binding specifically to the NF-$AT_p$ site, the ability to associate with c-Fos and C-Jun to form the NF-$AT_p$-Fos-Jun ternary complex on the NF-$AT_p$ site oligonucleotide, and the ability to act as a substrate for calcineurin.

Using another cloning strategy, synthetic degenerate oligonucleotides corresponding to stretches of 10–20 amino acid residues of NF-$AT_p$ can be made using an oligonucleotide synthesizer. These oligonucleotides can be used as hybridization probes to screen a cDNA library as described above. Positive clones can be sequenced, the sequence compared to the known amino acid sequence, and functional activity encoded by these DNAs tested as described above.

The gene encoding NF-$AT_p$ can also be identified using expression cloning techniques. In this case, the binding of NF-$AT_p$-specific antisera or monoclonal antibodies can be used to screen an expression library. Antibodies can be raised in an animal, for example, a rabbit, using as immunogens purified fragments of NF-$AT_p$ obtained as described above. These antibodies are labeled with a suitable label and are then used as probes to screen an expression library, e.g., a bacteriophage λ expression library generated by cloning cDNA from cells previously determined to express NF-$AT_p$. Positive clones are identified based on NF-$AT_p$-specific antibody binding. Clones identified in this manner can be isolated, sequenced and tested as described above.

What is claimed is:

1. An isolated DNA encoding a naturally occurring mammalian NF-$AT_p$ (preexisting component of nuclear factor of activated T cells).

2. The isolated DNA of claim 1, wherein said DNA encodes murine NF-$AT_p$.

3. The isolated DNA of claim 1, wherein said DNA encodes a protein which comprises the amino acid sequence of SEQ ID NO:5.

4. The isolated DNA of claim 1, wherein said DNA comprises the DNA sequence of FIG. 21 (SEQ ID NO:20).

5. The isolated DNA of claim 1, wherein said DNA encodes a protein which binds to the DNA sequence GCCCAAAGAGGAAAATTTGTTTCATACAG (SEQ ID NO:1), and which comprises the amino acid sequence of SEQ ID NO: 12.

6. The isolated DNA of claim 1, comprising the DNA sequence of FIG. 17 (SEQ ID NO:11), FIG. 21 (SRQ ID NO:20), or FIG. 22 (SEQ ID NO:19), wherein said DNA encodes a protein that binds the DNA sequence GCCCAAAGAGGAAAATTTGTTTCATACAG (SEQ ID NO:1).

7. The isolated DNA of claim 1, wherein said DNA comprises the sequence shown in FIG. 17 (SEQ ID NO:11) or FIG. 22 (SEQ ID NO:19).

8. The isolated DNA of claim 1, wherein said DNA comprises the nucleotide sequence shown in FIG. 17 (SEQ ID NO:11).

9. The isolated DNA of claim 1, wherein said DNA hybridizes under stringent conditions to a probe having a sequence consisting of SEQ ID NO:11.

10. A vector comprising the isolated DNA of claim 1.

11. A cell containing the isolated DNA of claim 1.

12. A method of manufacturing NF-$AT_p$, said method comprising culturing the cell of claim 11 under conditions permitting the expression of said DNA.

13. An isolated DNA comprising 20 nucleotides, wherein a strand of said DNA hybridizes under stringent conditions to a strand of the DNA of claim 1.

14. The isolated DNA of claim 13, wherein said DNA encodes a segment of NF-$AT_p$ which binds Fos-Jun or Jun—Jun.

15. The isolated DNA of claim 1, wherein said DNA comprises a 20 nucleotide segment of the DNA sequence of FIG. 21 (SEQ ID NO:20).

16. A method for detecting expression of NF-$AT_p$ in a cell, which method comprises contacting the mRNA of said cell with a hybridization probe comprising a 20 nucleotide, single-stranded, antisense segment of the isolated DNA of claim 1, and detecting hybridization of Said probe with said mRNA.

* * * * *

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
( A ) LENGTH: 29

( B ) TYPE: nucleic acid
( C ) STRANDEDNESS: single
( D ) TOPOLOGY: linear ( x i ) SEQUENCE DESCRIPTION: SEQ ID NO: 1:

GCCCAAAGAG GAAAATTTGT TTCATACAG 29

( 2 ) INFORMATION FOR SEQ ID NO: 2:

( i ) SEQUENCE CHARACTERISTICS:
( A ) LENGTH: 29
( B ) TYPE: nucleic acid
( C ) STRANDEDNESS: single
( D ) TOPOLOGY: linear ( x i ) SEQUENCE DESCRIPTION: SEQ ID NO: 2:

GCCCAAAGAG GAAAATTTGT TTATATCAG 29

( 2 ) INFORMATION FOR SEQ ID NO: 3:

( i ) SEQUENCE CHARACTERISTICS:
( A ) LENGTH: 29
( B ) TYPE: nucleic acid
( C ) STRANDEDNESS: single
( D ) TOPOLOGY: linear ( x i ) SEQUENCE DESCRIPTION: SEQ ID NO: 3:

GCCCAAAGAG GAAAATGGAC TTCATACAG 29

( 2 ) INFORMATION FOR SEQ ID NO: 4:

( i ) SEQUENCE CHARACTERISTICS:
( A ) LENGTH: 29
( B ) TYPE: nucleic acid
( C ) STRANDEDNESS: single
( D ) TOPOLOGY: linear ( x i ) SEQUENCE DESCRIPTION: SEQ ID NO: 4:

GCCCAAAGAC CTTAATTTGT TTCATACAG 29

( 2 ) INFORMATION FOR SEQ ID NO: 5:

( i ) SEQUENCE CHARACTERISTICS:
( A ) LENGTH: 890
( B ) TYPE: amino acid
( C ) STRANDEDNESS:
( D ) TOPOLOGY: linear ( x i ) SEQUENCE DESCRIPTION: SEQ ID NO: 5:

```
Gly Ser Ser Ala Ser Phe Ile Ser Asp Thr Phe Ser Pro Tyr Thr Ser
  1             5                  10                  15

Pro Cys Val Ser Pro Asn Asn Ala Gly Pro Asp Asp Leu Cys Pro Gln
             20                  25                  30

Phe Gln Asn Ile Pro Ala His Tyr Ser Pro Arg Thr Ser Pro Ile Met
         35                  40                  45

Ser Pro Arg Thr Ser Leu Ala Glu Asp Ser Cys Leu Gly Arg His Ser
     50                  55                  60

Pro Val Pro Arg Pro Ala Ser Arg Ser Ser Ser Pro Gly Ala Lys Arg
 65                  70                  75                  80

Arg His Ser Cys Ala Glu Ala Leu Val Ala Pro Leu Pro Ala Ala Ser
                 85                  90                  95

Pro Gln Arg Ser Arg Ser Pro Ser Pro Gln Pro Ser Pro His Val Ala
            100                 105                 110

Pro Gln Asp Asp Ser Ile Pro Ala Gly Tyr Pro Pro Thr Ala Gly Ser
```

-continued

```
        115                  120                  125

Ala Val Leu Met Asp Ala Leu Asn Thr Leu Ala Thr Asp Ser Pro Cys
    130                  135                  140

Gly Ile Pro Ser Lys Ile Trp Lys Thr Ser Pro Asp Pro Thr Pro Val
145                  150                  155                  160

Ser Thr Ala Pro Ser Lys Ala Gly Leu Ala Arg His Ile Tyr Pro Thr
                165                  170                  175

Val Glu Phe Leu Gly Pro Cys Glu Gln Glu Glu Arg Arg Asn Ser Ala
            180                  185                  190

Pro Glu Ser Ile Leu Leu Val Pro Pro Thr Trp Pro Lys Gln Leu Val
        195                  200                  205

Pro Ala Ile Pro Ile Cys Ser Ile Pro Val Thr Ala Ser Leu Pro Pro
    210                  215                  220

Leu Glu Trp Pro Leu Ser Asn Gln Ser Gly Ser Tyr Glu Leu Arg Ile
225             230                     235                  240

Glu Val Gln Pro Lys Pro His His Arg Ala His Tyr Glu Thr Glu Gly
                245                  250                  255

Ser Arg Gly Ala Val Lys Ala Pro Thr Gly Gly His Pro Val Val Gln
            260                  265                  270

Leu His Gly Tyr Met Glu Asn Lys Pro Leu Gly Leu Gln Ile Phe Ile
        275                  280                  285

Gly Thr Ala Asp Glu Arg Ile Leu Lys Pro His Ala Phe Tyr Gln Val
    290                  295                  300

His Arg Ile Thr Gly Lys Thr Val Thr Thr Thr Ser Tyr Glu Lys Ile
305                  310                  315                  320

Val Gly Asn Thr Lys Val Leu Glu Ile Pro Leu Glu Pro Lys Asn Asn
                325                  330                  335

Met Arg Ala Thr Ile Asp Cys Ala Gly Ile Leu Lys Leu Arg Asn Ala
            340                  345                  350

Asp Ile Glu Leu Arg Lys Gly Glu Thr Asp Ile Gly Arg Lys Asn Thr
        355                  360                  365

Arg Val Arg Leu Val Phe Arg Val His Val Pro Glu Pro Ser Gly Arg
    370                  375                  380

Ile Val Ser Leu Gln Ala Ala Ser Asn Pro Ile Glu Cys Ser Gln Arg
385                  390                  395                  400

Ser Ala His Glu Leu Pro Met Val Glu Arg Gln Asp Met Asp Ser Cys
                405                  410                  415

Leu Val Tyr Gly Gly Gln Gln Met Ile Leu Thr Gly Gln Asn Phe Thr
            420                  425                  430

Ala Glu Ser Lys Val Val Phe Met Glu Lys Thr Thr Asp Gly Gln Gln
        435                  440                  445

Ile Trp Glu Met Glu Ala Thr Val Asp Lys Asp Lys Ser Gln Pro Asn
    450                  455                  460

Met Leu Phe Val Glu Ile Pro Glu Tyr Arg Asn Lys His Ile Arg Val
465                  470                  475                  480

Pro Val Lys Val Asn Phe Tyr Val Ile Asn Gly Lys Arg Lys Arg Ser
                485                  490                  495

Gln Pro Gln His Phe Thr Tyr His Pro Val Pro Ala Ile Lys Thr Glu
            500                  505                  510

Pro Ser Asp Glu Tyr Glu Pro Ser Leu Ile Cys Ser Pro Ala His Gly
        515                  520                  525

Gly Leu Gly Ser Gln Pro Tyr Tyr Pro Gln His Pro Met Leu Ala Glu
    530                  535                  540
```

-continued

Ser Pro Ser Cys Leu Val Ala Thr Met Ala Pro Cys Gln Gln Phe Arg
545 550 555 560

Ser Gly Leu Ser Ser Pro Asp Ala Arg Tyr Gln Gln Gln Ser Pro Ala
565 570 575

Ala Ala Leu Tyr Gln Arg Ser Lys Ser Leu Ser Pro Gly Leu Leu Gly
580 585 590

Tyr Gln Gln Pro Ser Leu Leu Ala Ala Pro Leu Gly Leu Ala Asp Ala
595 600 605

His Arg Ser Val Leu Val His Ala Gly Ser Gln Gly Gln Gly Gln Gly
610 615 620

Ser Thr Leu Arg His Thr Ser Ser Ala Ser Gln Gln Ala Ser Pro Val
625 630 635 640

Ile His Tyr Ser Pro Thr Asn Gln Gln Leu Arg Gly Gly Gly His Gln
645 650 655

Glu Phe Gln His Ile Met Tyr Cys Glu Asn Phe Gly Pro Ser Ser Ala
660 665 670

Arg Pro Gly Pro Pro Pro Ile Asn Gln Gly Gln Arg Leu Ser Pro Gly
675 680 685

Ala Tyr Pro Thr Val Ile Gln Gln Gln Thr Ala Pro Ser Gln Arg Ala
690 695 700

Ala Lys Asn Gly Pro Ser Asp Gln Lys Glu Ala Leu Pro Thr Gly Val
705 710 715 720

Thr Val Lys Gln Glu Gln Asn Leu Asp Gln Thr Tyr Leu Asp Asp Ala
725 730 735

Ala Thr Ser Glu Ser Trp Val Gly Thr Glu Arg Tyr Ile Glu Arg Lys
740 745 750

Phe Trp Lys Lys Thr Leu Val Gln Pro Gly Leu Leu Pro Ser Phe Leu
755 760 765

Leu Leu Gly Ser Leu Ser Ala Gly Pro Arg Ser Gln Thr Pro Ser Glu
770 775 780

Arg Lys Pro Ile Glu Glu Asp Val Pro Leu Ser Cys Ser Gln Ile Ala
785 790 795 800

Trp Cys Cys Gln His Pro Leu Gly Thr Cys Pro Val Leu Pro Gly Pro
805 810 815

Leu Ala Val Glu Trp Trp Glu Gly Gln Leu Gly Arg Gly Leu Glu Pro
820 825 830

Ile Pro Trp Ala Pro Asp Ser Ala Gly Ser Leu His Glu Val Asp Ser
835 840 845

Val Gly Leu Ala Gly Val Val Gly Met Val Leu Leu Thr Leu Met His
850 855 860

His Phe Ser Met Asp Gln Asn Gln Thr Pro Ser Pro His Trp Gln Arg
865 870 875 880

His Lys Glu Val Ala Ser Pro Gly Trp Ile
885 890

( 2 ) INFORMATION FOR SEQ ID NO: 6:

( i ) SEQUENCE CHARACTERISTICS:
( A ) LENGTH: 18
( B ) TYPE: amino acid
( C ) STRANDEDNESS:
( D ) TOPOLOGY: linear ( x i ) SEQUENCE DESCRIPTION: SEQ ID NO: 6:

Met Arg Gly Ser His His His His His His Thr Ala Pro His Ala Ser
1 5 10 15

-continued

Ser Val ( 2 ) INFORMATION FOR SEQ ID NO: 7:

( i ) SEQUENCE CHARACTERISTICS:
( A ) LENGTH: 9
( B ) TYPE: amino acid
( C ) STRANDEDNESS:
( D ) TOPOLOGY: linear ( x i ) SEQUENCE DESCRIPTION: SEQ ID NO: 7:

Val Asp Leu Glu Pro Ser Leu Ile Ser
1 5

( 2 ) INFORMATION FOR SEQ ID NO: 8:

( i ) SEQUENCE CHARACTERISTICS:
( A ) LENGTH: 732
( B ) TYPE: nucleic acid
( C ) STRANDEDNESS: double
( D ) TOPOLOGY: linear ( x i ) SEQUENCE DESCRIPTION: SEQ ID NO: 8:

GCGGCTCCTC TGCCAGCTTC ATTTCTGACA CCTTCTCCCC CTACACCTCG CCCTGCGTCT 60

CACCCAATAA CGCCGGGCCC GACGACCTGT GTCCCCAGTT TCAAAACATC CCTGCTCATT 120

ATTCCCCCAG AACCTCTCCA ATAATGTCAC CTCGAACCAG CCTCGCCGAG GACAGCTGCC 180

TGGGCCGACA CTCGCCCGTG CCCCGTCCGG CATCCCGCTC CTCCTCACCC GGTGCCAAGC 240

GGAGGCATTC GTGCGCAGAG GCTTTGGTTG CTCCTCTGCC CGCAGCCTCA CCCCAGCGCT 300

CCCGGAGCCC CTCGCCACAG CCCTCGCCTC ACGTGGCACC GCAGGACGAC AGCATCCCCG 360

CTGGGTACCC CCCCACGGCC GGCTCTGCTG TTCTCATGGA TGCCCTCAAC ACCCTGGCCA 420

CCGACTCGCC CTGCGGGATC CCCTCCAAGA TATGGAAGAC CAGTCCTGAC CCGACGCCTG 480

TGTCCACCGC TCCGTCCAAG GCTGGCCTGG CCCGCCACAT CTACCCTACT GTGGAGTTCC 540

TGGGGCCATG TGAGCAGGAG GAGAGGAGGA ATTCCGCTCC AGAGTCCATC CTGCTGGTAC 600

CACCTACTTG GCCCAAGCAG TTGGTGCCGG CCATTCCCAT CTGCAGCATC CCTGTGACTG 660

CATCCCTCCC ACCACTCGAG TGGCCACTCT CCAATCAGTC GGGCTCCTAT GAGCTACGGA 720

TTGAGGTCCA AC 732

( 2 ) INFORMATION FOR SEQ ID NO: 9:

( i ) SEQUENCE CHARACTERISTICS:
( A ) LENGTH: 33
( B ) TYPE: nucleic acid
( C ) STRANDEDNESS: single
( D ) TOPOLOGY: linear ( x i ) SEQUENCE DESCRIPTION: SEQ ID NO: 9:

CGTTCGGATC CAGTGTTYAT GGAGAARACT ACA 33

( 2 ) INFORMATION FOR SEQ ID NO: 10:

( i ) SEQUENCE CHARACTERISTICS:
( A ) LENGTH: 34
( B ) TYPE: nucleic acid
( C ) STRANDEDNESS: single
( D ) TOPOLOGY: linear ( x i ) SEQUENCE DESCRIPTION: SEQ ID NO: 10:

CGACAGGAT CCTGYTGNATN ACNGTNGGRT ANGC 34

-continued ( 2 ) INFORMATION FOR SEQ ID NO: 11:

( i ) SEQUENCE CHARACTERISTICS:
( A ) LENGTH: 1065 base pairs
( B ) TYPE: nucleic acid
( C ) STRANDEDNESS: both
( D ) TOPOLOGY: both ( x i ) SEQUENCE DESCRIPTION: SEQ ID NO:11:

```
GCATACCCCG ATGATGTCCT GGACTATGGC CTCAAGCCAT ACAGCCCCCT TGCTAGTCTC    60
TCTGGCGAGC CCCCCGGCCG ATTCGGAGAG CCGGATAGGG TAGGGCCGCA GAAGTTTCTG   120
AGCGCGGCCA AGCCAGCAGG GGCCTCGGGC CTGAGCCCTC GGATCGAGAT CACTCCGTCC   180
CACGAACTGA TCCAGGCAGT GGGGCCCCTC CGCATGAGAG ACGCGGGCCT CCTGGTGGAG   240
CAGCCCCCCC TGGCCGGGGT GGCCGCCAGC CCGAGGTTCA CCCTGCCCGT GCCCGGCTTC   300
GAGGGCTACC GCCAGCCGCT TTGCTTGAGC CCCGCTAGCA GCGGCTCCTC TGCCAGCTTC   360
ATTTCTGACA CCTTCTCCCC CTACACCTGC CCCTGCGTCT CGCCCAATAA CGGCGGGCCC   420
GACGACCTGT GTCCGCAGTT TCAAAACATC CCTGCTCATT ATTCCCCCAG AACCTCGCCA   480
ATAATGTCAC CTCGAACCAG CTCGCCGAGG ACAGCTGCCT GGGCCGCCAC TCGCCCGTGC   540
CCCGTCCGGC CTCCCGCTCC TCATCGCCTG GTGCCAAGCG GAGGCATTCG TGCGCCGAGG   600
CCTTGGTTGC CCTGCCGCCC GGAGCCTCAC CCCAGCGCTC CCGGAGCCCC TCGCCGCAGC   660
CCTCATCTCA CGTGGCACCC CAGGACCACG GCTCCCCGGC TGGGTACCCC CCTGTGGCTG   720
GCTCTGCCGT GATCATGGAT GCCCTGAACA GCCTCGCCAC GGACTCGCCT TGTGGATCCC   780
CCCCAAGATG TGGAAGACCA GCCCTGACCC CTCGCCGGTG TCTCGCGCCC CATCCAAGGC   840
GGCCTGCCTC GCCACATCTA CCCGGCCGTG GAGTTCCTGG GGCTGCGAGC AGGGCGAGAG   900
GAGAAACTCG GCTCCAGAAT CCATCCTGCT GGTTCCGCCC ACTTGCCCAA GCCGCTGGTG   960
CCTGCCATTC CCATCTCGAC GATCCCATGA GCTCGATCCC TCCCTCACTT GAGTGGCCGC  1020
TGTCCAGTCA GTCATCGCGT TACGAGCTGC GGATCGAGGT GCAGC                  1065
```

( 2 ) INFORMATION FOR SEQ ID NO: 12:

( i ) SEQUENCE CHARACTERISTICS:
( A ) LENGTH: 357
( B ) TYPE: amino acid
( C ) STRANDEDNESS:
( D ) TOPOLOGY: linear ( x i ) SEQUENCE DESCRIPTION: SEQ ID NO: 12:

```
Ala Tyr Pro Asp Asp Val Leu Asp Tyr Gly Leu Lys Pro Tyr Ser Pro
  1               5                  10                  15

Leu Ala Ser Leu Ser Gly Glu Pro Pro Gly Arg Phe Gly Glu Pro Asp
             20                  25                  30

Arg Val Gly Pro Gln Lys Phe Leu Ser Ala Ala Lys Pro Ala Gly Ala
         35                  40                  45

Ser Gly Leu Ser Pro Arg Ile Glu Ile Thr Pro Ser His Glu Leu Ile
     50                  55                  60

Gln Ala Val Gly Pro Leu Arg Met Arg Asp Ala Gly Leu Leu Val Glu
 65                  70                  75                  80

Gln Pro Pro Leu Ala Gly Val Ala Ala Ser Pro Arg Phe Thr Leu Pro
                 85                  90                  95

Val Pro Gly Phe Glu Gly Tyr Arg Gln Pro Leu Cys Leu Ser Pro Ala
            100                 105                 110

Ser Ser Gly Ser Ser Ala Ser Phe Ile Ser Asp Thr Phe Ser Pro Tyr
        115                 120                 125
```

-continued

Thr Cys Pro Cys Val Ser Pro Asn Asn Gly Gly Pro Asp Asp Leu Cys
130 135 140

Pro Gln Phe Gln Asn Ile Pro Ala His Tyr Ser Pro Arg Thr Ser Pro
145 150 155 160

Ile Met Ser Pro Arg Thr Ser Leu Ala Glu Asp Ser Cys Leu Gly Arg
165 170 175

His Ser Pro Val Pro Arg Pro Ala Ser Arg Ser Ser Ser Pro Gly Ala
180 185 190

Lys Arg Arg His Ser Cys Ala Glu Ala Leu Val Ala Leu Pro Pro Gly
195 200 205

Ala Ser Pro Gln Arg Ser Arg Ser Pro Ser Pro Gln Pro Ser Ser His
210 215 220

Val Ala Pro Gln Asp His Gly Ser Pro Ala Gly Tyr Pro Pro Val Ala
225 230 235 240

Gly Ser Ala Val Ile Met Asp Ala Leu Asn Ser Leu Ala Thr Asp Ser
245 250 255

Pro Cys Gly Ile Pro Pro Lys Met Trp Lys Thr Ser Pro Asp Pro Ser
260 265 270

Pro Val Ser Arg Ala Pro Ser Lys Ala Gly Leu Pro Arg His Ile Tyr
275 280 285

Pro Ala Val Glu Phe Leu Gly Pro Cys Glu Gln Gly Glu Arg Arg Asn
290 295 300

Ser Ala Pro Glu Ser Ile Leu Leu Val Pro Pro Thr Trp Pro Lys Pro
305 310 315 320

Leu Val Pro Ala Ile Pro Ile Ser Thr Ile Pro Xaa Ala Arg Ser Leu
325 330 335

Pro Pro Leu Glu Trp Pro Leu Ser Ser Gln Ser Ser Arg Tyr Glu Leu
340 345 350

Arg Ile Glu Val Gln
355

( 2 ) INFORMATION FOR SEQ ID NO: 13:

( i ) SEQUENCE CHARACTERISTICS:
( A ) LENGTH: 60
( B ) TYPE: nucleic acid
( C ) STRANDEDNESS: double
( D ) TOPOLOGY: linear ( x i ) SEQUENCE DESCRIPTION: SEQ ID NO: 13:

GGATGACGCA GCCACTTCAG AAAGCTGGGT TGGGACAGAA AGGTATATAG AGAGAAAATT 60

( 2 ) INFORMATION FOR SEQ ID NO: 14:

( i ) SEQUENCE CHARACTERISTICS:
( A ) LENGTH: 52
( B ) TYPE: nucleic acid
( C ) STRANDEDNESS: double
( D ) TOPOLOGY: linear ( x i ) SEQUENCE DESCRIPTION: SEQ ID NO: 14:

GGATGACGAG TTGATAGACA CACACCTTAG CTGGATACAA AACATATTAT GA 52

( 2 ) INFORMATION FOR SEQ ID NO: 15:

( i ) SEQUENCE CHARACTERISTICS:
( A ) LENGTH: 60
( B ) TYPE: nucleic acid
( C ) STRANDEDNESS: double
( D ) TOPOLOGY: linear ( x i ) SEQUENCE DESCRIPTION: SEQ ID NO: 15:

GGATGACGTT AATGAAATCA TCAGGAAGGA GTTTTCAGGA CCTCCCTCCC GAAATCAGAC 60

( 2 ) INFORMATION FOR SEQ ID NO: 16:

( i ) SEQUENCE CHARACTERISTICS:
( A ) LENGTH: 16
( B ) TYPE: amino acid
( C ) STRANDEDNESS:
( D ) TOPOLOGY: linear ( x i ) SEQUENCE DESCRIPTION: SEQ ID NO: 16:

Asp Asp Ala Ala Thr Ser Glu Ser Trp Val Gly Thr Glu Arg Tyr Ile
1 5 10 15

( 2 ) INFORMATION FOR SEQ ID NO: 17:

( i ) SEQUENCE CHARACTERISTICS:
( A ) LENGTH: 16
( B ) TYPE: amino acid
( C ) STRANDEDNESS:
( D ) TOPOLOGY: linear ( x i ) SEQUENCE DESCRIPTION: SEQ ID NO: 17:

Asp Asp Glu Leu Ile Asp Thr His Leu Ser Trp Ile Gln Asn Ile Leu
1 5 10 15

( 2 ) INFORMATION FOR SEQ ID NO: 18:

( i ) SEQUENCE CHARACTERISTICS:
( A ) LENGTH: 20
( B ) TYPE: amino acid
( C ) STRANDEDNESS:
( D ) TOPOLOGY: linear ( x i ) SEQUENCE DESCRIPTION: SEQ ID NO: 18:

Asp Asp Val Asn Glu Ile Ile Arg Lys Glu Phe Ser Gly Pro Pro Ser
1 5 10 15

Arg Asn Gln Thr
20

( 2 ) INFORMATION FOR SEQ ID NO: 19:

( i ) SEQUENCE CHARACTERISTICS:
( A ) LENGTH: 114
( B ) TYPE: nucleic acid
( C ) STRANDEDNESS: double
( D ) TOPOLOGY: linear ( x i ) SEQUENCE DESCRIPTION: SEQ ID NO: 19:

ATGGGCTCAT CAACTTCATC AAGCAGCAGC GCGAGGCCAG AGTCCAATAA ACTCGTGCTC 60

ATCTGCAGCC TCCTCTGTGA CTCCCCTTCT CTTCTCGTCC CTCCTCCCCG GAGC 114

( 2 ) INFORMATION FOR SEQ ID NO: 20:

( i ) SEQUENCE CHARACTERISTICS:
( A ) LENGTH: 2675
( B ) TYPE: nucleic acid
( C ) STRANDEDNESS: double
( D ) TOPOLOGY: linear ( x i ) SEQUENCE DESCRIPTION: SEQ ID NO: 20:

GCGGCTCCTC TGCCAGCTTC ATTTCTGACA CCTTCTCCCC CTACACCTCG CCCTGCGTCT 60

CACCCAATAA CGCCGGGCCC GACGACCTGT GTCCCCAGTT TCAAAACATC CCTGCTCATT 120

-continued

| | | | | | | |
|---|---|---|---|---|---|---|
| ATTCCCCCAG | AACCTCTCCA | ATAATGTCAC | CTCGAACCAG | CCTCGCCGAG | GACAGCTGCC | 180 |
| TGGGCCGACA | CTCGCCCGTG | CCCCGTCCGG | CATCCCGCTC | CTCCTCACCC | GGTGCCAAGC | 240 |
| GGAGGCATTC | GTGCGCAGAG | GCTTTGGTTG | CTCCTCTGCC | CGCAGCCTCA | CCCCAGCGCT | 300 |
| CCCGGAGCCC | CTCGCCACAG | CCCTCGCCTC | ACGTGGCACC | GCAGGACGAC | AGCATCCCCG | 360 |
| CTGGGTACCC | CCCCACGGCC | GGCTCTGCTG | TTCTCATGGA | TGCCCTCAAC | ACCCTGGCCA | 420 |
| CCGACTCGCC | CTGCGGGATC | CCCTCCAAGA | TATGGAAGAC | CAGTCCTGAC | CCGACGCCTG | 480 |
| TGTCCACCGC | TCCGTCCAAG | GCTGGCCTGG | CCCGCCACAT | CTACCCTACT | GTGGAGTTCC | 540 |
| TGGGGCCATG | TGAGCAGGAG | GAGAGGAGGA | ATTCCGCTCC | AGAGTCCATC | CTGCTGGTAC | 600 |
| CACCTACTTG | GCCCAAGCAG | TTGGTGCCGG | CCATTCCCAT | CTGCAGCATC | CCTGTGACTG | 660 |
| CATCCCTCCC | ACCACTCGAG | TGGCCACTCT | CCAATCAGTC | GGGCTCCTAT | GAGCTACGGA | 720 |
| TTGAGGTCCA | ACCCAAGCCC | CATCACCGGG | CCCACTATGA | GACGGAGGGC | AGCCGTGGCG | 780 |
| CTGTCAAAGC | CCCAACAGGA | GGACACCCTG | TGGTGCAGCT | CCACGGCTAC | ATGGAGAACA | 840 |
| AGCCTCTGGG | GCTTCAGATC | TTCATTGGGA | CAGCAGATGA | GAGGATCCTT | AAGCCGCACG | 900 |
| CCTTCTACCA | AGTACACAGG | ATCACTGGGA | AAACGGTCAC | CACCACGAGC | TATGAGAAGA | 960 |
| TCGTAGGCAA | CACCAAGGTC | CTGGAGATCC | CCCTGGAGCC | AAAGAACAAC | ATGAGAGCCA | 1020 |
| CCATCGACTG | TGCAGGCATC | CTGAAGCTCC | GAAACGCTGA | CATCGAGCTG | CGGAAGGGCG | 1080 |
| AGACGGACAT | CGGCAGGAAG | AACACGCGTG | TGCGCCTGGT | GTTCCGCGTG | CACGTCCCAG | 1140 |
| AGCCCAGTGG | GCGCATCGTC | TCCCTGCAGG | CTGCGTCCAA | CCCCATCGAG | TGCTCTCAGC | 1200 |
| GCTCTGCCCA | CGAGCTGCCC | ATGGTGGAGA | GACAAGACAT | GGACAGCTGC | CTGGTCTACG | 1260 |
| GGGGCCAGCA | GATGATCCTC | ACGGGCCAGA | ACTTCACAGC | GGAGTCCAAG | GTTGTGTTCA | 1320 |
| TGGAGAAGAC | TACAGATGGG | CAGCAGATTT | GGGAGATGGA | AGCTACGGTG | GATAAAGACA | 1380 |
| AGAGCCAGCC | TAACATGCTT | TTTGTTGAGA | TCCCCGAGTA | TCGGAACAAG | CACATCCGCG | 1440 |
| TGCCCGTGAA | AGTCAACTTC | TACGTCATCA | ACGGAAAGAG | GAAACGAAGT | CAGCCACAGC | 1500 |
| ACTTTACCTA | CCACCCAGTC | CCTGCCATCA | AGACAGAGCC | CAGCGATGAG | TATGAACCAT | 1560 |
| CTTTGATCTG | CAGCCCCGCC | CATGGAGGCC | TGGGGAGCCA | GCCATATTAC | CCACAGCACC | 1620 |
| CAATGCTGGC | CGAGTCCCCC | TCCTGCCTTG | TGGCTACCAT | GGCCCCCTGC | CAACAGTTCC | 1680 |
| GCTCGGGGCT | CTCATCCCCC | GATGCTCGCT | ACCAACAGCA | GAGCCCCGCA | GCTGCCCTCT | 1740 |
| ACCAGAGAAG | CAAGAGCCTG | AGTCCCGGCC | TGCTGGGCTA | CCAGCAGCCG | TCCCTCCTGG | 1800 |
| CAGCACCCTT | GGGTCTGGCT | GATGCCCACC | GCTCTGTGCT | GGTGCATGCT | GGTTCTCAGG | 1860 |
| GGCAGGGGCA | GGGCTCCACC | CTCCGACACA | CATCCTCGGC | CAGCCAGCAG | GCCTCACCCG | 1920 |
| TGATCCACTA | CTCACCCACC | AACCAGCAGC | TTCGCGGTGG | GGGTCACCAG | GAGTTCCAGC | 1980 |
| ATATCATGTA | CTGTGAAAAC | TTCGGCCCCA | GCTCTGCCAG | GCCTGGCCCG | CCTCCCATCA | 2040 |
| ACCAAGGTCA | GAGGCTGAGC | CCGGGCGCCT | ACCCCACAGT | CATCCAACAA | CAGACTGCCC | 2100 |
| CGAGCCAAAG | AGCTGCCAAA | AACGGACCCA | GTGACCAGAA | GGAAGCTCTG | CCCACGGGAG | 2160 |
| TGACCGTCAA | ACAGGAACAG | AACCTGGACC | AGACCTACCT | GGATGACGCA | GCCACTTCAG | 2220 |
| AAAGCTGGGT | TGGGACAGAA | AGGTATATAG | AGAGAAAATT | TTGGAAGAAG | ACCCTTGTGC | 2280 |
| AGCCTGGGCT | CCTGCCCTCA | TTTTTACTTC | TTGGCTCCCT | GTCTGCTGGA | CCAAGGTCAC | 2340 |
| AGACACCATC | AGAAAGAAAG | CCCATAGAGG | AAGACGTGCC | CTTGAGTTGC | AGCCAGATAG | 2400 |
| CCTGGTGTTG | TCAGCATCCC | TTGGGGACCT | GCCCTGTCCT | GCCAGGGCCT | TTAGCTGTAG | 2460 |
| AGTGGTGGGA | AGGGCAGCTC | GGGCGTGGGC | TGGAGCCAAT | TCCCTGGGCT | CCAGACAGTG | 2520 |

-continued

CCGGCAGCCT CCATGAGGTG GACAGTGTAG GCCTGGCGGG AGTGGTCGGA ATGGTTCTGC 2580

TCACTCTTAT GCACCACTTC TCCATGGATC AGAACCAGAC CCCCTCTCCT CACTGGCAAA 2640

GGCACAAAGA GGTTGCTAGC CCAGGCTGGA TCTGA 2675

( 2 ) INFORMATION FOR SEQ ID NO: 21:

( i ) SEQUENCE CHARACTERISTICS:
( A ) LENGTH: 732
( B ) TYPE: nucleic acid
( C ) STRANDEDNESS: double
( D ) TOPOLOGY: linear ( x i ) SEQUENCE DESCRIPTION: SEQ ID NO: 21:

GCGGCTCCTC TGCCAGCTTC ATTTCTGACA CCTTCTCCCC CTACACCTGC CCCTGCGTCT 60

CGCCCAATAA CGGCGGGCCC GACGACCTGT GTCCGCAGTT TCAAAACATC CCTGCTCATT 120

ATTCCCCCAG AACCTCGCCA ATAATGTCAC CTCGAACCAG CNTCGCCGAG GACAGCTGCC 180

TGGGCCGCCA CTCGCCCGTG CCCCGTCCGG CCTCCCGCTC CTCATCGCCT GGTGCCAAGC 240

GGAGGCATTC GTGCGCCGAG GCCTTGGTTG CCCTGCCGCC CGGAGCCTCA CCCCAGCGCT 300

CCCGGAGCCC CTCGCCGCAG CCCTCATCTC ACGTGGCACC CCAGGACCAC GGCTCCCCGG 360

CTGGGTACCC CCCTGTGGCT GGCTCTGCTG TGATCATGGA TGCCCTGAAC AGCCTCGCCA 420

CGGACTCGCC TTGTGGNATC CCCCCCAAGA TGTGGAAGAC CAGTCCTGAC CCCTCGCCGG 480

TGTCTCGCGC CCCATCCAAG GCNGGCCTGC CTCGCCACAT CTACCCGGCC GTGGAGTTCC 540

TGGGGCNNTG CGAGCAGGGC GAGAGGAGAA ACTCGGCTCC AGAATCCATC CTGCTGGTTC 600

CGCCCACTTG NCCCAAGCCG CTGGTGCCTG CCATTCCCAT CTCGACGATC CCATGAGCTC 660

GATCCCTCCC TNCACTTGAG TGGCCGCTGT CCAGTCAGTC ATCGCGTTAC GAGCTGCGGA 720

TCGAGGTGCA GC 732